United States Patent
Lin et al.

(10) Patent No.: US 8,993,256 B2
(45) Date of Patent: Mar. 31, 2015

(54) FUSION PROTEINS AND POLYNUCLEOTIDE CONSTRUCTS TO MEASURE PROTEIN TURN-OVER

(75) Inventors: Michael Z. Lin, San Diego, CA (US); Roger Y. Tsien, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 871 days.

(21) Appl. No.: 12/443,411

(22) PCT Filed: Sep. 28, 2007

(86) PCT No.: PCT/US2007/021077
§ 371 (c)(1),
(2), (4) Date: Mar. 27, 2009

(87) PCT Pub. No.: WO2008/054595
PCT Pub. Date: May 8, 2008

(65) Prior Publication Data
US 2010/0041092 A1      Feb. 18, 2010

Related U.S. Application Data

(60) Provisional application No. 60/848,125, filed on Sep. 28, 2006.

(51) Int. Cl.
*C12Q 1/02* (2006.01)
*C12N 9/00* (2006.01)
*C12N 9/48* (2006.01)
*C12N 1/20* (2006.01)
*C12N 15/00* (2006.01)
*C07H 21/04* (2006.01)
*C12Q 1/37* (2006.01)
*G01N 33/58* (2006.01)

(52) U.S. Cl.
CPC .............. *C12Q 1/37* (2013.01); *G01N 33/582* (2013.01)
USPC .......... 435/29; 435/183; 435/212; 435/252.3; 435/320.1; 536/23.2

(58) Field of Classification Search
None
See application file for complete search history.

(56) References Cited

U.S. PATENT DOCUMENTS 5,643,758 A * 7/1997 Guan et al. .................. 435/69.7

OTHER PUBLICATIONS

Ciruela. Curr Opin Biotechnol. Aug. 2008;19(4):338-43. Epub Jul. 16, 2008.*
Canals et al. J Neurochem. Feb. 2008;88(3):726-34.*
Zheng et al. J Biol Chem. Jan. 14, 2011;286(2):1277-82. Epub Nov. 8, 2010.*
Kim et al. Protein Expr Purif. Mar. 2005;40(1):107-17.*
Fronda, Christian L., The International Search Report and the Written Opinion of the International Searching Authority, PCT/US07/21077, mailed Sep. 29, 2008.
Pestka, Sidney, "Introduction of Protein Kinase Recognition Sites into Proteins: A Review of Their Preparation, Advantages, and Applications." Protein Expression and Purification, 1999, pp. 203-214.
Szweda, Piotr, Cloning, Expression, and Purification of the *Staphylococcus simulans* Lysostaphin Using the Intein-Chitin-Binding Domain (CBD) System, Protein Expression and Purification, 2001, pp. 467-471.
Wu, Xiaoli, "Measurement of Two Caspase Activities Simultaneously in Living Cells by a Novel Dual FRET Fluorescent Indicator Probe." Cytometry Part A, 2006, pp. 477-486.
Lindner, Nora, International Preliminary Report on Patentability and Written Opinion, Date of Issuance of Report: Mar. 31, 2009, International Application No. PCT/US07/21077.

* cited by examiner

*Primary Examiner* — Christian Fronda
(74) *Attorney, Agent, or Firm* — Joseph R. Baker, Jr.; Gavrilovich, Dodd & Lindsey LLP

(57) ABSTRACT

The disclosure provides method and compositions for visualizing protein turnover. In particular, the disclosure provides methods and compositions useful for measuring the age of particular proteins or the dynamics of localized protein translation.

10 Claims, 18 Drawing Sheets

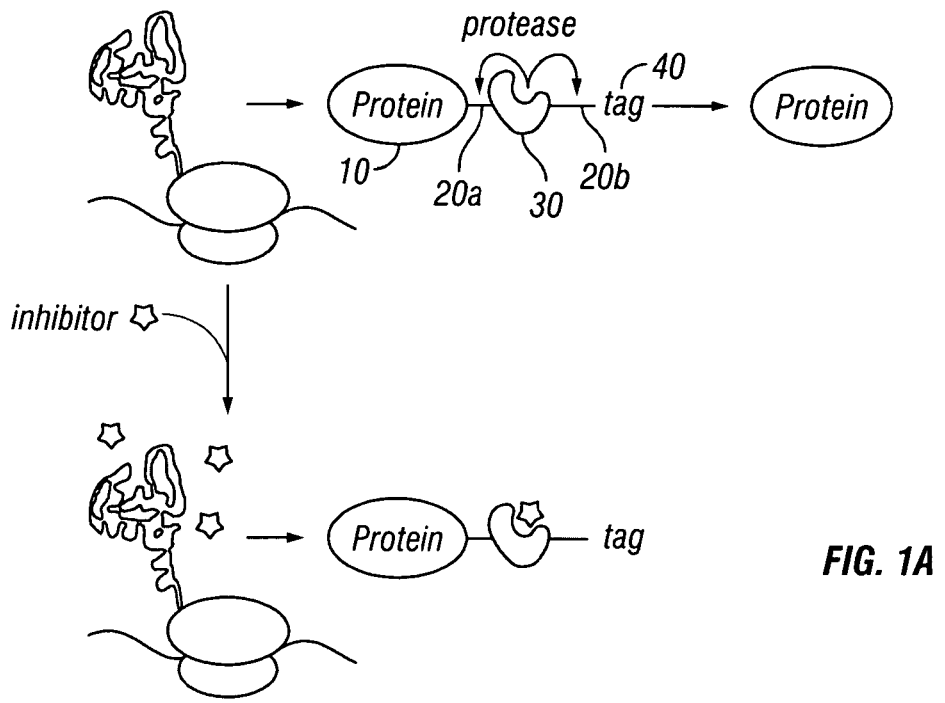
FIG. 1A
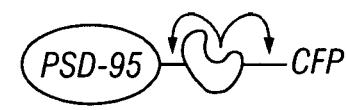
μM BILN-2061: 0 1 10
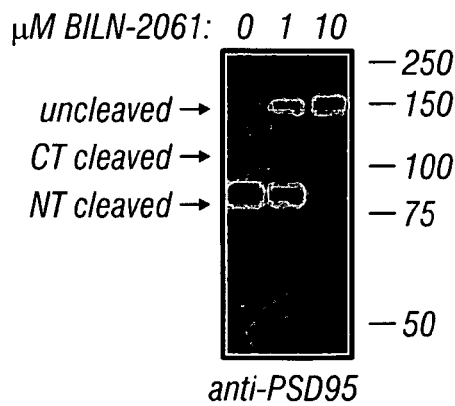
anti-PSD95
FIG. 1B

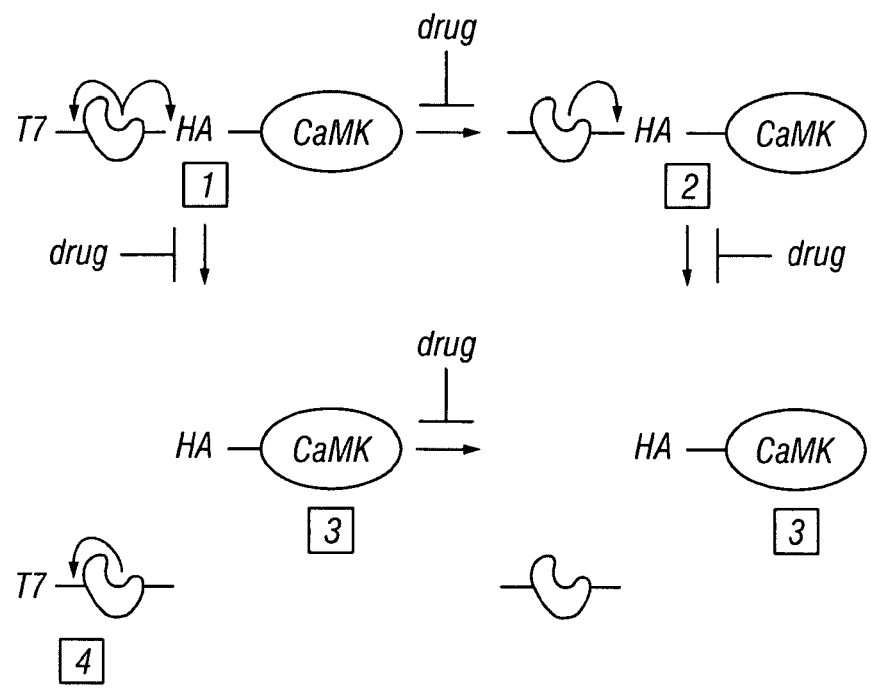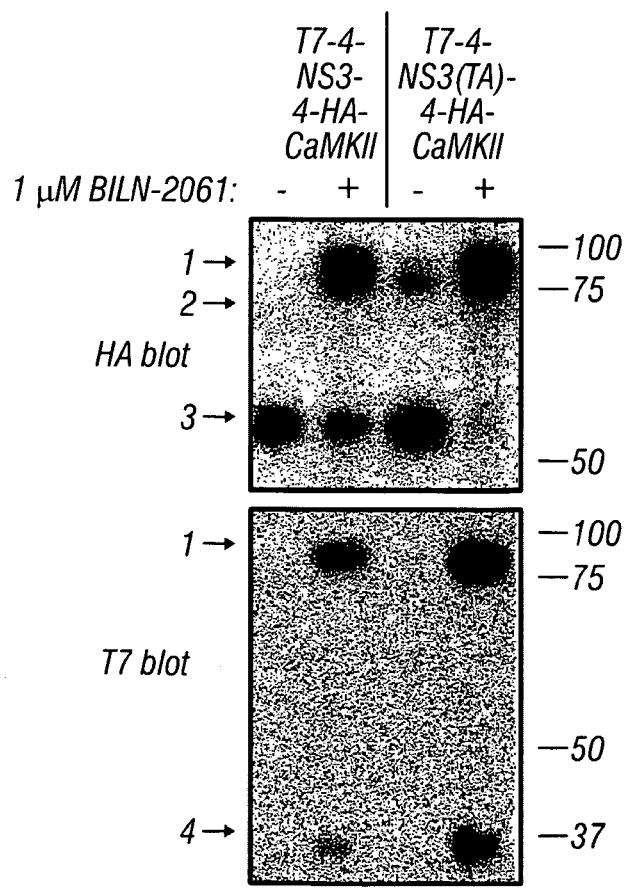
FIG. 1D-2 maximum PSD-95 IF
(arbitrary units)
A (untransfected): 3669
B (transfected): 2835

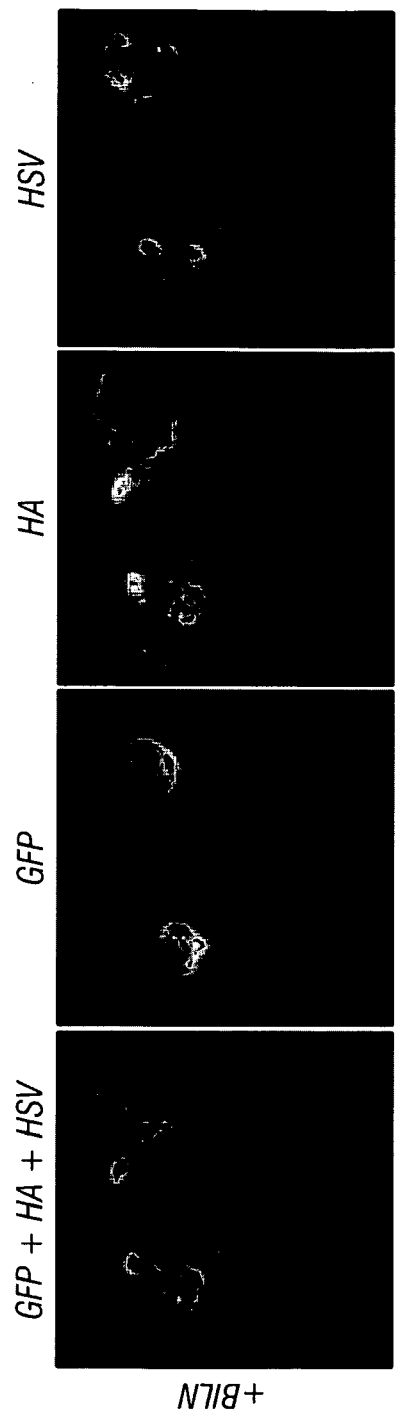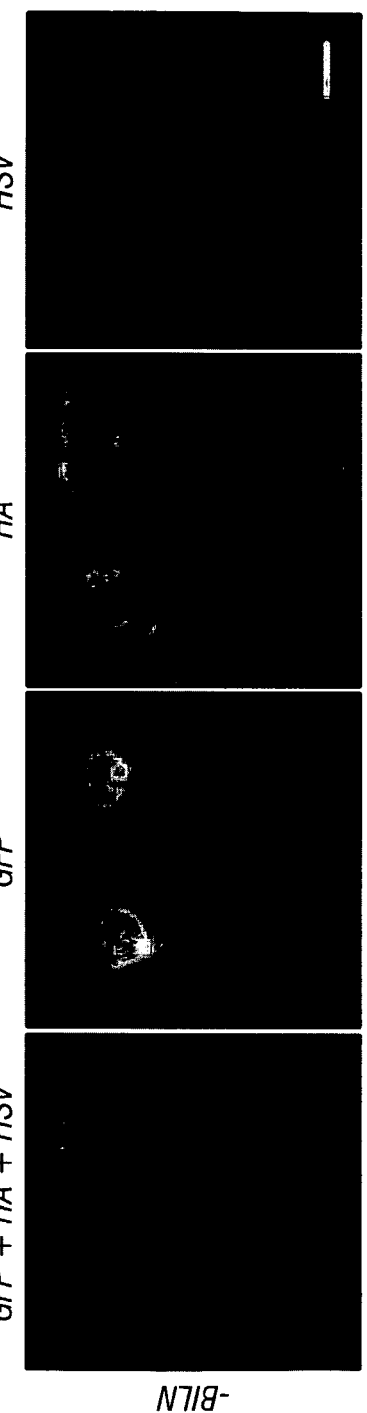
FIG. 4A
FIG. 4B

*anti-PSD95*

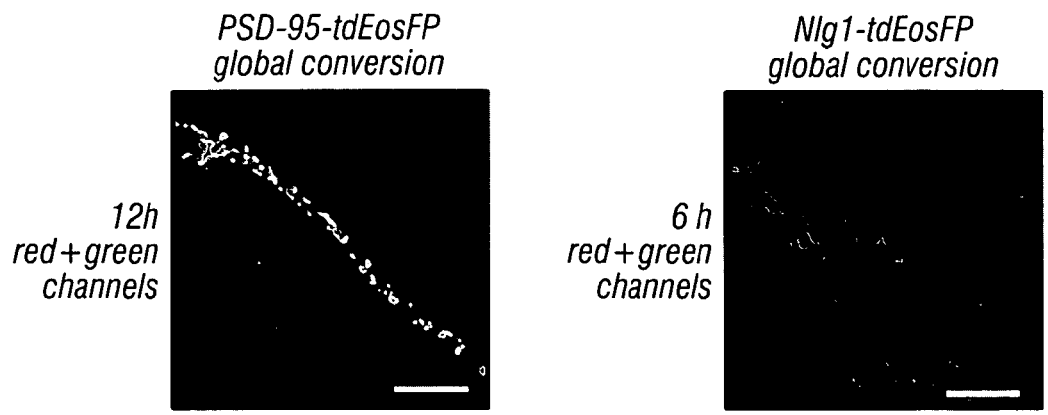
FIG. 8A  FIG. 8B
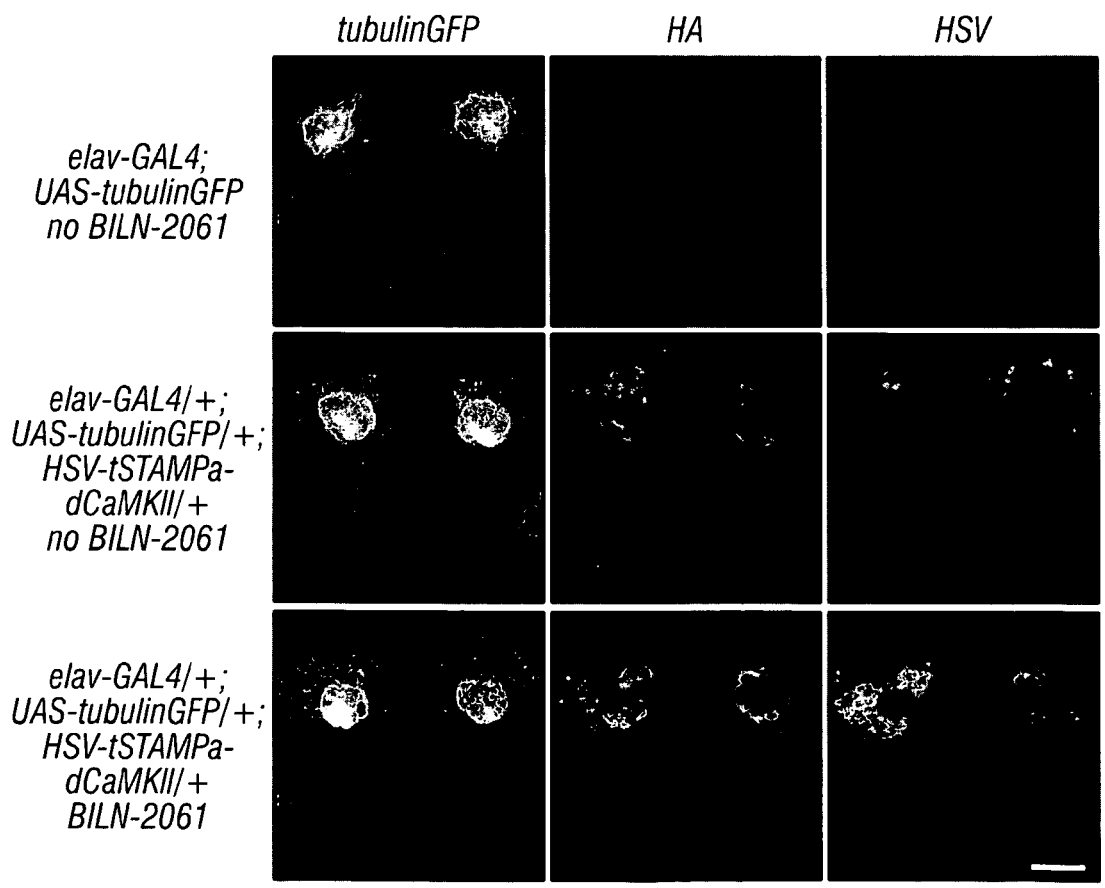
FIG. 9

FUSION PROTEINS AND POLYNUCLEOTIDE CONSTRUCTS TO MEASURE PROTEIN TURN-OVER

CROSS REFERENCE TO RELATED APPLICATIONS

This application claims priority under 35 U.S.C. 371 to International Application Number PCT/US07/21077, filed Sep. 28, 2007, which application claims priority under 35 U.S.C. §119 from Provisional Application Ser. No. 60/848,125, filed Sep. 28, 2006, the disclosure of which is incorporated herein by reference.

STATEMENT AS TO FEDERALLY SPONSORED RESEARCH

The invention was made with government support under Grant No. NS27177 awarded by the National Institutes of Health. The government has certain rights in the invention.

FIELD OF THE INVENTION

The disclosure provides method and compositions for monitoring protein turnover and controlling protein behaviors. In particular, the disclosure provides methods and compositions useful for measuring the age of particular proteins or the dynamics of localized protein translation as well as protein behaviors including, but not limited to, protein localization and stability.

BACKGROUND

Control over protein synthesis and degradation rates is involved in the regulation of most biological processes and is believed to be the primary cause of numerous diseases. Regulation of the synthesis rates of biomolecules in living systems is one of the most fundamental features of biochemical and physiologic control. For this reason, measurement of biosynthetic and degradation rates in vivo has been the subject of enormous research effort over the past 50 years. Among the macromolecules that have been studied, proteins have received perhaps the most intense attention due to their central role in controlling biological processes. The measurement of protein synthesis has traditionally required the use of isotopic labels (stable isotopes or radioisotopes).

Spatially controlled protein production and directed delivery of newly synthesized proteins are fundamental processes in the development, maintenance, and adaptation of specialized cellular structures. Local protein synthesis allows for the rapid production of proteins in regions of the cell where they are needed. For example, spatially localized protein translation is associated with myofibril growth in cardiac myocytes (Larsen and Saetersdal, 1998) and contributes to actin production at the leading edge of migrating fibroblasts (Huttelmaier et al., 2005; Rodriguez et al., 2006). In neurons, local protein production is especially important in establishing the complex architecture of the cell and in restricting activity-dependent changes to subsets of synapses. During neuronal development, guidance of axons to their targets involves the localized induction of translation in the axonal growth cone by extracellular factors (Leung et al., 2006; Wu et al., 2005). In mature neurons, distal dendrites locally synthesize proteins in response to neuronal pathway stimulation or local application of growth factors or neurotransmitters (Ouyang et al., 1999; Steward and Worley, 2002; Aakalu et al., 2001; Ju et al., 2004; Kacharmina et al., 2000; Muddashetty et al., 2007; Smith et al., 2005; Todd et al., 2003). The induction of long-term potentiation (LTP), an electrophysiological model of learning, induces the redistribution of polyribosomes to sites near synapses and the enlargement of a polyribosome-associated subset of synapses (Harris et al., 2003; Ostroff et al., 2002), and dendritic translation is required for LTP and learning (Bradshaw et al., 2003; Miller et al., 2003). These results suggest that activity-dependent local protein synthesis may contribute to synapse growth during learning. Interestingly, the Fragile X mental retardation protein FMRP is required for stimulus-induced translation of a subset of dendritic messages (Muddashetty et al., 2007), implying that abnormalities in activity-dependent local protein synthesis may underlie some disorders of mental cognition as well.

Delivery of newly synthesized proteins to subcellular regions by various protein trafficking mechanisms is also essential in maintaining specialized cellular functions. For example, protein sorting within the secretory pathway allows for long-distance transport of proteins from their site of synthesis at the endoplasmic reticulum to discrete final destinations within the cell. This process is necessary for the establishment and maintenance of polarized epithelial cells and of axonal and dendritic specializations in neurons, including pre- and postsynaptic complexes (Horton and Ehlers, 2003; Horton et al., 2005; Muth and Caplan, 2003). Aside from the well studied processes of protein trafficking and local protein translation, protein delivery to specific subsets of structures in cells could conceivably occur due to spatially localized demands for particular proteins. For example, in neurons, synapses undergoing potentiation or growth can be expected to accumulate recently synthesized structural proteins at higher rates than stable synapses. Incorporation of molecules from regional pools of recently synthesized proteins by specific synapses would represent a step in protein delivery distinct from protein trafficking or activity-dependent local protein synthesis. In the case of proteins that arrive in dendrites by trafficking or local synthesis, accumulation in specific "receptive" synapses could represent a subsequent final step in spatially regulated protein delivery.

SUMMARY

In order to allow sensitive protein tagging in deep tissues of living animals in a time-controllable manner, the disclosure provides a protein tag whose presence can be induced by a one-time administration of a small molecule agent or drug. In one aspect, a composition of the disclosure incorporates a specific protease activity to confer self-removing behavior onto an epitope tag and then to use a corresponding protease inhibitor to block tag removal. Proteins synthesized after inhibitor application, which can occur at a time of the experimenter's choosing, will remain tagged.

The disclosure provides a fusion construct, comprising: (i) a polypeptide of interest, (ii) a cleavage agent, (iii) a cleavable linker, and (iv) a tag moiety, wherein each of (i-iv) are operably linked, and wherein the cleavage agent can be inhibited by contacting with an inhibitor. In one aspect, the tag is selected from the group consisting of an epitope tag, a fluorescent moiety, a fluorescent moieties that undergo FRET, BRET (bioluminescence resonant energy transfer) moieties through the assembly of an acceptor fluorophore with a bioluminescence protein (luciferase), a radioactive moiety, a radiopaque moiety, a paramagnetic moiety, a nanoparticle, a vesicle, a molecular beacon, a marker, a marker enzyme, a contrast agent, a chemotherapeutic agent, a radiation-sensitizer, a peptide or protein that affects the cell cycle, and a protein toxin. In another aspect, the cleavage agent is a protease. The cleavable linker can comprise a peptide cleavable by a protease. In one embodiment, the composition has the general structure, with reference to the numerals above: (i)-(iii)-(ii)-(iii)-(iv); (iv)-(iii)-(ii)-(iii)-(i); (i)-(iii)-(ii)-(iv); (iv)-(ii)-(iii)-(i); (i)-(ii)-(iii)-(iv); or (iv)-(iii)-(ii)-(i). Wherein the tag comprises fragments that when reassembled for a detectable moeity, the composition, for example, can have the structure: (i)-(iv-frag$_1$)-(ii)-(iii)-(iv-frag$_2$); (i)-(iv-frag$_1$)-(ii)-(iii)-(iv-frag$_2$); (i)-(iii)-(iv-frag$_1$)-(ii)-(iii)-(iv-frag$_2$); (i)-(iv-frag$_1$)-(iii)-(ii)-(iv-frag$_2$); (iv-frag$_1$)-(ii)-(iii)-(iv-frag$_2$)-(i); (iv-frag$_1$)-(iii)-(ii)-(iii)-(iv-frag$_2$)-(i); (iv-frag$_1$)-(iii)-(ii)-(iv-frag$_2$)-(i); and (iv-frag$_2$)-(iii)-(ii)-(iii)-(iv-frag$_1$)-(i). In one aspect, the inhibitor is a protease inhibitor.

The disclosure also provide a fusion polypeptide, comprising: (i) a polypeptide of interest, (ii) a cleavage agent, (iii) a cleavable linker, and (iv) a tag moiety, wherein each of (i)-(iv) are operably linked, and wherein the cleavage agent can be inhibited by contacting with an inhibitor. In one aspect, the tag is selected from the group consisting of an epitope tag, a fluorescent moiety, a fluorescent moieties that undergo FRET, a bioluminescent moiety, a bioluminescent moiety that undergoes BRET, a peptide or protein that affects the cell cycle, a marker enzyme, and a protein toxin. In another aspect, the tag moiety is chemically conjugated to the fusion polypeptide. In a further aspect, where the tag is chemically conjugated the tag moiety is selected from the group consisting of a radioactive moiety, a radiopaque moiety, a paramagnetic moiety, a nanoparticle, a vesicle, a molecular beacon, a contrast agent, a chemotherapeutic agent, and a radiation-sensitizer. In another aspect, the cleavage agent is a protease. In yet another aspect, when the cleavable linker comprises a peptide the cleavable agent is a protease. With reference to the roman numerals above (i.e., i-iv), the fusion polypeptide can be ordered as follows: (i)-(iii)-(ii)-(iii)-(iv); (i)-(iii)-(ii)-(iv); (iv)-(iii)-(ii)-(iii)-(i); (iv)-(iii)-(ii)-(i); (i)-(ii)-(iii)-(iv) or (iv)-(ii)-(iii)-(i). In one aspect, the cleavage agent cleaves a linker between the polypeptide of interest and the cleavage agent. In another aspect, the cleavage agent cleaves a linker between the tag and the cleavage agent. In yet another aspect, the inhibitor is a protease inhibitor.

The disclosure also provides a polynucleotide encoding a fusion polypeptide as described herein.

The disclosure provides an isolated polynucleotide comprising: a multiple cloning site; a nucleic acid encoding a first linker moiety; a nucleic acid encoding a cleavage agent; a nucleic acid encoding a second linker moiety; and a nucleic acid tag moiety. In one aspect, the polynucleotide further comprises a nucleic acid encoding a polypeptide of interest. In another aspect, the first and second linker moieties comprise cleavable linker peptides. In a further aspect, the first or second linker moiety comprises a cleavable linker peptide. The first and second linker moieties can be the same or different. In another aspect, tag is selected from the group consisting of an epitope tag, a fluorescent moiety, complementary fluorescent moiety fragments, a fluorescent moiety that undergoes FRET, a bioluminescent moiety, complementary bioluminescent moiety fragments, a bioluminescent moiety that undergoes BRET, a peptide or protein that affects cell signaling or the cell cycle, a marker enzyme, a marker enzyme fragment, and a protein toxin.

The disclosure also provides a host cell transfected with the polynucleotide of the disclosure.

The disclosure provides a method of monitoring protein turnover or protein age of a polypeptide of interest, comprising (a) contacting a cell or subject with a polypeptide or polynucleotide of the disclosure; (b) measuring an amount of tag or a property of a tag in the cell or subject; (c) contacting the cell or subject with an inhibitor of the cleavable agent; (d) measuring an amount of tag or a property of a tag in the cell or subject after contacting with the cleavable agent; comparing the measurements of (b) and (d), wherein a change is indicative of protein turnover or protein age.

The disclosure also provides a construct, comprising: (i) a molecule of interest, (ii) a cleavage agent, (iii) a cleavable linker, and (iv) a tag moiety, wherein each of (i-iv) are operably linked, and wherein the cleavage agent can be inhibited by contacting with an inhibitor. In one aspect, the molecule of interest comprises a nanoparticle, a polypeptide, a peptide, or a nucleic acid.

The disclosure also provides kits comprising a TimeSTAMP polypeptide or polynucleotide of the disclosure, compartmentalized for use.

BRIEF DESCRIPTION OF THE DRAWINGS

FIG. 4A-B shows drug-regulated epitope tagging in living flies. (A) BILN-2061 controls epitope tagging in flies. Adult flies expressing HSV-TimeSTAMPt-HA-dCaMKII and tubulin-GFP in neurons were administered BILN-2061, then brains were analyzed by immunocytochemistry 6 hours later. HSV labelling for newly synthesized dCaMKII is present in the mushroom bodies (MBs) in the presence of BILN-2061. Note HA staining reveals total dCaMKII is expressed in the MBs with enrichment in the distal lobes. (B) No HSV staining is observed in flies not administered BILN-2061. Maximum intensity projections of confocal sections spaced 5 µm apart throughout the fly brain are shown. Scale bars, 20 µm.

FIG. 8A-B shows a validation of protein movements using the photoconvertible protein tdEosFP. (A) After PSD-95-tdEosFP in 12 DIV neurons was photoconverted globally to red, new green protein was observed in a gradient from the cell body 12 hours later, confirming results obtained by TimeSTAMP. (B) Similarly, 6 hours after photoconversion, new Nlg1-tdEosFP protein was observed in the soma in a perinuclear distribution consistent with movement through the secretory pathway. Scale bars, 20 µm.

FIG. 9 shows drug-regulated epitope tagging in living flies expressing slow-cleaving TimeSTAMP. BILN-2061 controls epitope tagging. Adult flies expressing HSV-TimeSTAMPa-HA-dCaMKII and tubulin-GFP in neurons were fed yeast paste with 500 µM BILN-2061, then brains were analyzed by immunocytochemistry 6 hours later. HA labels all dCaMKII, while HSV labelling is responsive to BILN-2061. Coronal confocal sections through the calyx of the MB are shown. Scale bar, 20 µm.

DETAILED DESCRIPTION

Figure 1C:
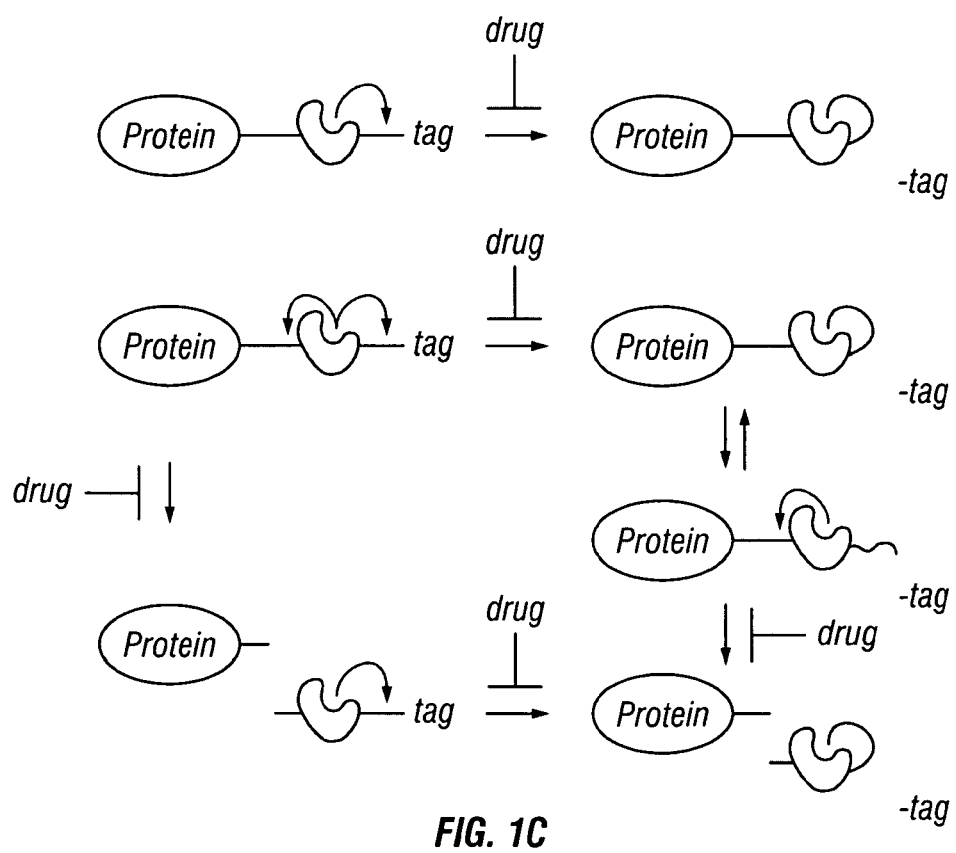
FIG. 1A-E shows an exemplary construct for "TimeSTAMP" and implementation of the disclosure. (A) Strategy for drug-dependent epitope tagging of newly synthesized proteins. (B) PSD-95 fused to the TimeSTAMPa module, comprising an N-terminal epitope tag, an NS4A/B protease site, an NS3 protease domain with a T54A mutation, another NS4A/B site, and cyan fluorescent protein (CFP), is efficiently processed to release the protease and CFP in the absence of the NS3 protease inhibitor BILN-2061. In the continual presence of BILN-2061, cleavage at both sites is efficiently inhibited. (C) Shows additional exemplary schematics of the disclosure. (D) Shows an embodiment of the disclosure. (E) Shows the tag that is removed by the action of a protease is a degradation signal (degron). The action of the protease removes the degron in the absence of protease inhibitor. In the presence of inhibitor, the degron remains linked to the protein of interest and the protein is rapidly degraded. The immunoblot of the protein of interest demonstrates that its expression level can be modulated in a dose-dependent manner by protease inhibitors.

As used herein and in the appended claims, the singular forms "a," "and," and "the" include plural referents unless the context clearly dictates otherwise. Thus, for example, reference to "a polypeptide" includes a plurality of such polypeptides and reference to "the nucleic acid" includes reference to one or more nucleic acids and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed throughout the text are provided solely for their disclosure prior to the filing date of the present application. Nothing herein is to be construed as an admission that the inventors are not entitled to antedate such disclosure by virtue of prior disclosure.

Rapid control over protein function is highly desirable, both for potential applications in gene therapy and in investigative research settings. The use of proteins expressed from genes (gene therapy) is a topic of active investigation. One major problem in gene therapy is the development of methods for tight control of protein function, for example to control protein activity levels for optimal therapeutic effect or to stop production when it would be inappropriate or harmful. Turning down or turning off protein expression by changing the activity of factors controlling gene transcription is slow, requiring up to 24 hours to take full effect. Methods for shutting off protein expression more rapidly would be highly desirable. In addition, expression of proteins encoded by transgenes is commonly performed to investigate protein function in research settings. For example, researchers often express transgenic hyperactive or dominant-interfering forms of an endogenous protein, or simply overexpress the native form of the protein, and observe resulting cellular changes to deduce the function of the protein. Synchronous and rapid control of the onset of activity of transgenically encoded proteins is desirable in this setting in order to be able to observe the immediate effects of protein activity on the cell, for example if the expected cellular response changes with time or if adaptation, downstream effects, or toxicity occurs. Methods to sequester proteins away from their sites of activity in a manner that can be temporally regulated by a drug, or to link a protein to a domain that can repress its function in a manner that can be temporally regulated by a drug, would allow for rapid regulation of protein function and would therefore be highly desirable.

Spatial regulation of synaptic protein turnover, including local protein synthesis and degradation, is believed to play a crucial role in the structural plasticity of synapses and in the maintenance of long-term potentiation. Recently, studies of local protein turnover in cell culture have been facilitated by optical reporters of protein translation and methods for pulse-chase protein labeling. However, existing methods either do not recapitulate regulation of protein localization or other aspects of posttranslational control, or are difficult to adapt to living animals.

Destabilized versions of the green fluorescent protein GFP have been used as reporters of activity-dependent mRNA translation when translation is placed under the control of mRNA regulatory sequences of interest (Aakalu et al., 2001; Karpova et al., 2006). A fluorescent protein named "Fluorescent Timer" exhibits an emission spectrum that gradually shifts from green to red over time (Terskikh et al., 2000), due to increasing fluorescence energy transfer from green to red fluorescent subunits as red subunits appear (Verkhusha et al., 2004). Fusing proteins of interest to photoconvertible fluorescent proteins whose emission wavelengths can be irreversibly converted from green to red by intense short-wavelength light, such as Kaede, Eos, and Dendra, allows selective labelling of proteins synthesized after performing global photoconversion at a time of interest (Raab-Graham et al., 2006; Wiedenmann et al., 2004). Similarly, fluorescence recovery after photobleaching (FRAP) allows selective visualization of newly synthesized proteins after global photobleaching. Sequential application of fluorophore-conjugated chemicals that bind to a specific peptide motif, such as the green and red fluorescent dyes FlAsH and ReAsH, has also been used to study protein trafficking and turnover in living cells, including the movement of Gag protein during HIV budding (Rudner et al., 2005), the assembly of connexins in gap junctions (Gaietta et al., 2002), and activity-dependent translation of glutamate receptors in dendrites of cultured neurons (Ju et al., 2004).

However, existing methods are limited either in their fidelity for reporting newly synthesized proteins or in their compatibility with thick tissues or living animals. Destabilized GFP can serve only as a proxy reporter of translational activity and not as a generally applicable fusion tag. Fusions of destabilized GFP and a long-lived protein of interest would either lead either to stabilization of GFP or destabilization of the protein of interest. In the former case, GFP fluorescence would no longer be specific to new proteins, while in the latter case, rapid turnover of a protein may affect the function of signaling or structural complexes containing the protein of interest. Destabilized GFP is therefore unsuitable for revealing the actual localization or turnover behavior of proteins of interest. Fluorescent Timer has not seen application as a protein tag, likely due to its obligate tetrameric nature and uncontrollable time course of color change. Photoconvertible fluorescent proteins or FRAP require uniform delivery of high-intensity UV or violet light throughout the volume of interest, which will be impossible in intact opaque organisms, and rely on detection of a non-amplifiable fluorescence signal that requires time for maturation. The photoconverting irradiation can cause phototoxicity and already bleaches the red photoproduct significantly before photoconversion of the green precursor is complete. Methods based on wavelength changes in fluorescent proteins do not allow amplification or discrimination by non-optical methods. On the other hand, sequential chemical labeling technologies require stoichiometric binding of the first label followed by rapid washout and introduction of a second label, which is difficult in thick tissues and animals. Furthermore, labeling in intact cells by membrane-permeant dyes requires high levels of target protein expression coupled with extensive washing to reduce nonspecific binding (Johnson, Gaietta).

The disclosure provides compositions, methods and systems for epitope tagging of newly synthesized proteins with temporal control provided by a non-toxic cell permeable protease inhibitor ("TimeSTAMP"; for Time-Specific Tag for the Age Measurement of Proteins). TimeSTAMP refers to a fusion polypeptide construct of the disclosure as described more fully herein. The disclosure further provides polynucleotides encoding a TimeSTAMP construct, as well as vectors and cassettes.

A TimeSTAMP construct of the disclosure comprise distinct domains. For example, in order to allow sensitive protein tagging in deep tissues of living animals in a time-controllable manner, the disclosure provides a protein tag whose presence can be induced by a one-time administration of a small molecule agent or drug. In one aspect, a composition of the disclosure incorporates a specific protease activity to confer self-removing behavior onto an epitope tag and then to use a corresponding protease inhibitor to block tag removal. Proteins synthesized after inhibitor application, which can occur at a time of the experimenter's choosing, will remain tagged (FIG. 1A).

The disclosure provides a TimeSTAMP technique, a drug-controlled method for the time-specific tagging and age measurement of proteins with spatial specificity. This method has a high signal-to-noise ratio, can be used to tag proteins while preserving mechanisms of posttranslational regulation, and is compatible with slice preparations or freely behaving animals. The TimeSTAMP method can be used to visualize any number or protein molecules. For example, the TimeSTAMP can be used to measure the turnover of synaptic components at synapses under various stimulation conditions, and to perform retrospective analyses of the spatial distribution of synaptic growth events in intact neuronal networks.

The disclosure provides methods that allow a researcher to selectively detect copies of a protein of interest synthesized after a certain time of interest. This is particularly useful for visualizing protein turnover for the purpose of measuring the age of subcellular structure such as synapses, or for the studying of dynamics of protein translation, such as localized protein translation in subcellular compartments (e.g., dendrites and axons). Specifically, the disclosure is a self-removing genetically encoded tag whose removal can be blocked by an inhibitor agent (e.g., a small non-toxic drug).

In one aspect, the disclosure employs a self-removing tag and a small molecule agent or drug to block the cleavage of the tag. The tag can be fused to a polypeptide or nucleic acid or genetically engineered such that the polypeptide, or nucleic acid, and tag are operably linked following expression. Upon delivery or expression in a cell or animal, the tag will continuously remove itself. Upon addition of an inhibitor (e.g., a drug or small molecule), the tag will be preserved on proteins synthesized after the time of inhibitor addition. The tag can then be detected by any existing method for detecting polypeptides.

In one embodiment, a tag will be cleaved in the absence of a small molecule or inhibitor and retained after the time the small molecule or inhibitor is added. In addition to protein turnover and subcellular localization aspect, the disclosure can be used to modulate degradation or targeting of a protein of interest, where the drug preserves linkage of the protein to a domain conferring degradation or localization behavior. The disclosure overcomes the shortcomings described above and is also compatible with various immunological detection methods (blotting, cytochemistry, and the like) which allows for sensitive detection. As a method of controlling protein expression, the disclosure provides a single component system that is simpler than interrupting transcription or altering intermolecular interactions.

The disclosure provides a TimeSTAMP polypeptide comprising a binding agent or cognate linked to a cleavage agent which is linked to a detectable tag moiety. The binding agent or cognate can be linked to the cleavage agent by a cleavable linker. In some aspects, the cleavage agent is linked to the detectable tag moiety by a cleavable linker. In other aspects, both the binding agent or cognate and the detectable tag moiety are each linked to the cleavage agent by a cleavable linker. The activity of the cleavage agent can be inhibited by contacting the cleavage agent with an inhibitor.

The binding agent or cognate can be a receptor; ligand; antibody; substrate; modified ligands, antibodies or substrates; or any other member of a binding pair. In some aspect, the binding ligand or cognate irreversibly binds to its binding partner. In this aspect, a TimeSTAMP polypeptide comprises a fusion construct that upon exposure to its binding ligand partner or cognate partner interacts with the partner such that the fusion construct is linked to the partner thereby providing a bound-TimeSTAMP construct. In the presence of a cleavage agent inhibitor the bound-TimeSTAMP construct remains intact, however, upon removal of the cleavage agent inhibitor the cleavage agent cleaves a cleavable linker thus disrupting the bound-TimeSTAMP construct. The disruption can be detected by measuring a change in the detectable tag moiety or location.

A polynucleotide encoding a binding ligand or cognate operably linked to cleavage agent and a detectable tag moiety are also provided. The polynucleotide can be expressed by a cell upon transfection or transformation to monitor turn-over of, or lifetime of, the binding ligand's binding partner.

Figure 1D:
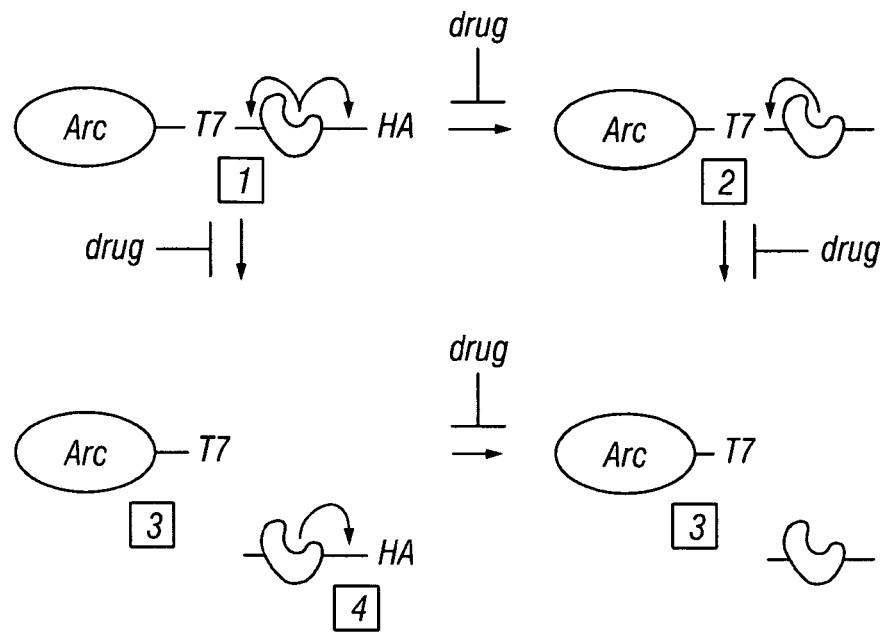
Figure 1:
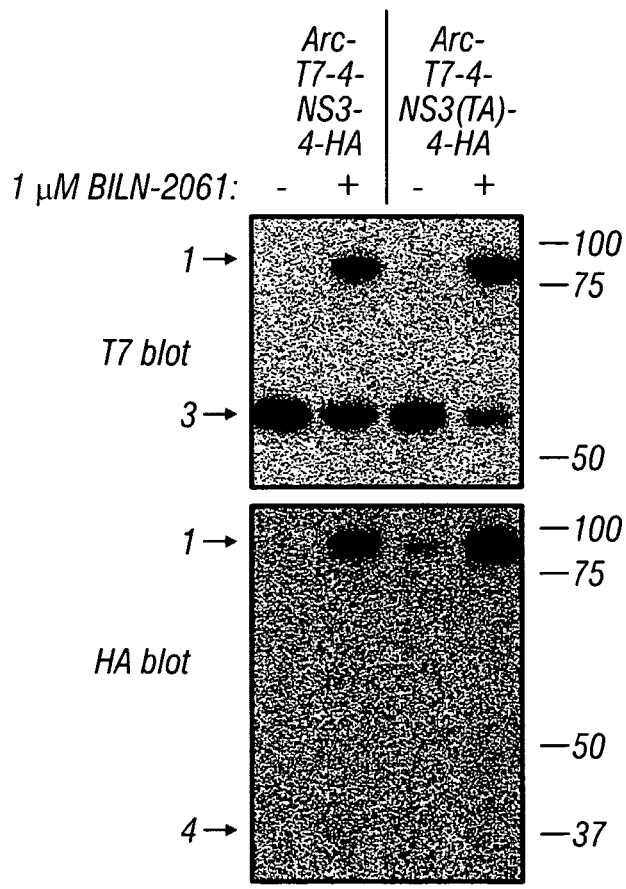
Figure 1E:
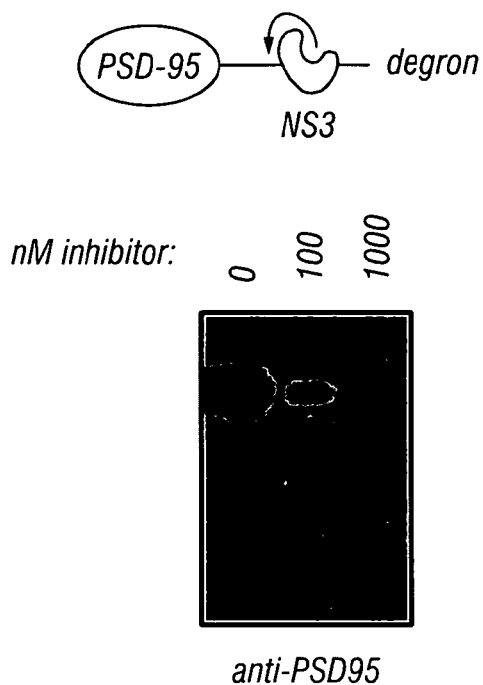

FIG. 1 provides another aspect of a TimeSTAMP composition and method of the disclosure. A molecule of interest 10 (e.g., a protein) is linked via linker 20a (e.g., a cleavable linker) to a cleavage agent 30 (e.g., a protease) which is linked via linker 20b (e.g., a cleavable linker) to a tag 40. Upon cleavage of a cleavable linker(s) 20a and/or 20b by cleavage agent 30, a detectable signal change can be identified via tag measurement.

In one embodiment, the composition has the general structure, with reference to the numerals above: 10-20-30-20-40; 40-20-30-20-10; 10-20-30-40; 40-30-20-10; 10-30-20-40; or 40-20-30-10. In one aspect, the inhibitor is a protease inhibitor.

A tag for purposes of the disclosure can include any molecule, material, substance, or construct that may be transported into a cell or expressed by a cell by linkage to a protein or nucleic acid of interest. Typically the tag will comprise a detectable moiety or signal. In one aspect, the tag will generate a first detectable signal or molecular weight when associated with the protein or nucleic acid of interest and a second different signal or molecular weight when not associated with the protein or nucleic acid of interest. A tag moiety may be, for example, an epitope tag, a fluorescent moiety, a fluorescent moiety that undergoes FRET, a fluorescent protein fragment, a bioluminescent moiety, a bioluminescent moiety that undergoes BRET (bioluminescence resonant energy transfer) through the assembly of an acceptor fluorophore with a bioluminescence protein (e.g., luciferase), a marker, a marker enzyme (e.g., horse-radish peroxidase (HRP), beta-galactosidase, or other enzyme suitable for marking a cell), an enzyme fragment, a contrast agent (e.g., for diagnostic imaging), a chemotherapeutic agent, a peptide or protein that affects cell signal transduction or the cell cycle, a protein toxin, or other tag suitable for transport into or expression by a cell. In one aspect, the tag is attached to the peptide linker for cleavage by a protease, and therefore is peptidic themselves or are conjugates to peptides. The tag could contain a radioactive, radiopaque, paramagnetic, nanoparticular, or vesicular moiety, or a contrast agent or chemotherapeutic agent, by conjugation of such a moiety to the main peptidic residue of the tag (either covalent or noncovalently).

In one aspect, the TimeSTAMP construct or fusion polypeptide of the disclosure can comprise a protein of interest linked to the N-terminal fragment of fluorescent protein, linked to a protease, which is linked to a C-terminal fragment of fluorescent protein. The fragments can be spaced from protease by a cleavable linker on either or both of the N'- or C'-terminal ends of the protease. In such an aspect, neither fragment fluoresces alone, but when the two fragments are in close proximity for minutes to hours, the fragments interact to fluoresce (e.g., reassemble into a fluorescent protein). Fluorescent fragments that can interact to form a fluorescent polypeptide are known in the art (see, e.g., Ozawa, Analyt. Chim. Acta, 556:58-68, 2006; and Michnick et al., Nat. Rev., 6:569-582, 2007; the disclosure of which are incorporated herein by reference). When a cleavage agent such as a protease is active (i.e., without inhibitor present), the cleavage agent (e.g., a protease) rapidly cuts apart the two fragments before they can reassemble, therefore there is no fluorescence. If, however, the inhibitor is present, the fragments are juxtaposed/interact together by the inert protease for sufficient long to generate fluorescence. Such fluorescence is associated with the molecule or polypeptide of interest. Thus the new protein copies made after inhibitor administration would be fluorescent, obviating the need to permeabilize the cells for antibody labeling (e.g., administer labeled antibody, then wash off unbound antibody etc.). In another embodiment, the polypeptide or protein of of interest is linked to the C-terminus of the fragment-protease-fragment cassette. In another aspect, a bioluminescent proteins such as luciferase can also be reassembled from their appropriate known fragments. Wherein when the tag comprises fragments that when they reassembled form a detectable moiety (e.g., fluorescent protein fragments), the composition, for example, can have the structure: 10-(40-frag$_1$)-30-20-(40-frag$_2$); 10-(40-frag$_1$)-20-30-20-(40-frag$_2$); 10-20-(40-frag$_1$)-30-20-(40-frag$_2$); 10-(40-frag$_1$)-20-30-(40-frag$_2$); (40-frag$_1$)-30-20-(40-frag$_2$)-10; (40-frag$_1$)-20-30-20-(40-frag$_2$)-10; (40-frag$_1$)-20-30-(40-frag$_2$)-10; and (40-frag$_2$)-20-30-20-(40-frag$_1$)-10.

In one embodiment, the tag can be a protein domain used to confer a behavior on the fused protein in a drug-induced manner. This behavior can be any domain-conferred behavior, including targeting to a subcellular structure and alternation of stability, e.g., by the recruitment of protein degradation machinery. Without drug, proteins will lose the domain and will not be subject to regulation by it. After addition of the drug, newly synthesized fusion proteins will retain the domain and be regulated.

In one aspect, a molecule of interest is operably linked to a linker that is in-turn linked to a protease, which is in-turn linked to linker and in-turn to a tag. Thus, the tag is linked by a cleavable substrate (e.g., protease cleavable peptide) to the molecule of interest. The linker at either end of the protease may be the same of different. In another aspect, the molecule of interest is linked to the tag via a cleavable linkage.

The terms "cleavage linkage", "cleavage site", or "protease site" refers to the bond cleaved by a protease or other agent (e.g. a scissile bond) and typically the surrounding three to four amino acids of either side of the bond, when the linkage is a peptide. Such peptide cleavable linkers can be engineered from the naturally existing sequence by at least one amino acid substitution.

The linker moiety is typically a peptide moiety, but can be another organic molecular moiety as well. In a one embodiment, the linker moiety includes a cleavage recognition site specific for an enzyme or other cleavage agent of interest. The cleavable linkage/linker may include, but is not limited to, a protease cleavable peptide substrate.

A cleavable linker is typically cleavable under physiological conditions. A cleavable linker typically comprises between about 2 to about 100 atoms, or between about 6 to about 30 atoms. Cleavable linkers include amino acid residues, and may be a peptide linkage of between about 1 to about 30, or between about 2 to about 10 amino acid residues. A cleavable linker suitable for the practice of the disclosure may be a flexible linker. For example, a cleavable linker suitable for the practice of the disclosure is a flexible linker, and may be about 6 to about 24 atoms in length. Proteases which can be used to cleave corresponding cleavable linkers are those that cleave sequences attached to the N- or C-termini of the protease. Such proteases are commonly found in viruses in which multiple different proteins are initially translated from a single long messenger RNA so that the different proteins need to be cut apart postranslationally. Examples of such proteases are hepatitis C viral protease and human immunodeficiency viral protease.

In addition, a cleavable linker may be configured for cleavage by an enzyme, such as a matrix metalloprotease (MMP). Other enzymes which may cleave a cleavable linker include, for example, urokinase plasminogen activator (uPA), lysosomal enzymes, cathepsins, prostate-specific antigen, Herpes simplex virus protease, cytomegalovirus protease, thrombin, caspase, and interleukin 1-beta converting enzyme. In other embodiments, a cleavable linker may include a S-S linkage, or may include a transition metal complex that falls apart when the metal is reduced.

When the cleavage agent is a protease, the linker can comprise a peptide containing a cleavage site for the protease. A cleavage site for a protease is a specific amino acid sequence recognized by the protease during proteolytic cleavage. The linker can contain any protease recognition motif known in the art or discovered in the future.

A cleavable linker may be designed for cleavage in the presence of particular conditions or in a particular environment. Cleavage of such a linker may, for example, be enhanced or may be effected by particular pathological signals or a particular environment in a tissue or cell.

A great deal is known about the substrate preferences of different MMPs, so that cleavable linker may be designed to be cleaved by individual members of the large MMP family of proteinases. The specific sequence of amino acids in the protease cleavage site depends on the catalytic mechanism of the protease, which is defined by the nature of the functional group at the protease's active site, as discussed above. The disclosure permits a great deal of flexibility and discretion in terms of the choice of the protease cleavable linker peptide. The protease specificity of the linker is determined by the amino acid sequence of the linker. Specific amino acid sequences can be selected in order to determine which protease will cleave the linker;

In one embodiment, the amino acid linker is linked by a peptide bond to the C-terminus of the N-terminal polypeptide of the cleavable agent or protease and via a peptide bond to the N-terminus of the C-terminal polypeptide of a molecule of interest or tag.

Some proteases useful according to the disclosure are discussed in the following references: V. Y. H. Hook, Proteolytic and cellular mechanisms in prohormone and proprotein processing, RG Landes Company, Austin, Tex., USA (1998); N. M. Hooper et al., Biochem. J. 321: 265-279 (1997); Z. Werb, Cell 91: 439-442 (1997); T. G. Wolfsberg et al., J. Cell Biol. 131: 275-278 (1995); K. Murakami and J. D. Etlinger, Biochem. Biophys. Res. Comm. 146: 1249-1259 (1987); T. Berg et al., Biochem. J. 307: 313-326 (1995); M. J. Smyth and J. A. Trapani, Immunology Today 16: 202-206 (1995); R. V. Talanian et al., J. Biol. Chem. 272: 9677-9682 (1997); and N. A. Thornberry et al., J. Biol. Chem. 272: 17907-17911 (1997), the disclosures of which are incorporated herein.

The following are examples of proteases which can be used to cleave corresponding cleavable linkers: signal peptidase; proprotein convertases of the subtilisin/kexin family (furin, PC1, PC2, PC4, PACE4, PC5, PC); proprotein convertases cleaving at hydrophobic residues (e.g., Leu, Phe, Val, or Met); proprotein convertases cleaving at small amino acid residues such as Ala or Thr; proopiomelanocortin converting enzyme (PCE); chromaffin granule aspartic protease (CGAP); prohormone thiol protease; carboxypeptidases (e.g., carboxypeptidase E/H, carboxypeptidase D and carboxypeptidase Z); aminopeptidases (e.g., arginine aminopeptidase, lysine aminopeptidase, aminopeptidase B); prolyl endopeptidase; aminopeptidase N; insulin degrading enzyme; calpain; high molecular weight protease; and, caspases 1, 2, 3, 4, 5, 6, 7, 8, and 9. Other proteases include, but are not limited to, aminopeptidase N; puromycin sensitive aminopeptidase; angiotensin converting enzyme; pyroglutamyl peptidase II; dipeptidyl peptidase IV; N-arginine dibasic convertase; endopeptidase 24.15; endopeptidase 24.16; amyloid precursor protein secretases alpha, beta and gamma; angiotensin converting enzyme secretase; TGF alpha secretase; TNF alpha secretase; FAS ligand secretase; TNF receptor-I and -II secretases; CD30 secretase; KL1 and KL2 secretases; IL6 receptor secretase; CD43, CD44 secretase; CD16-I and CD16-II secretases; L-selectin secretase; Folate receptor secretase; MMP 1, 2, 3, 7, 8, 9, 10, 11, 12, 13, 14, and 15; urokinase plasminogen activator; tissue plasminogen activator; plasmin; thrombin; BMP-1 (procollagen C-peptidase); ADAM 1, 2, 3, 4, 5, 6, 7, 8, 9, 10, and 11; and, granzymes A, B, C, D, E, F, G, and H.

In one aspect, an inhibitor (e.g., a small molecule or drug) is administered following expression or delivery of a TimeSTAMP composition of the disclosure. Upon delivery or administration of the inhibitor, cleavage of the cleavable linker by the cleavage agent is inhibited resulting in a detectable change in the TimeSTAMP composition. Such a change can be detected based upon, for example, a change in fluorescence based upon FRET, change in molecular weight by TOFMS or gel mobility shift, by ELISA (comprising antibodies to the tag or protein), histoimmunological techniques (useful for molecule localization), and the like.

In one aspect, the disclosure provides a fusion construct comprising an HCV NS3 protease and a tag on a protein of interest. The protease functions to continually cleave away the tag unless a protease inhibitor is present. FIG. 1C illustrates two implementations of the disclosure (the protease is the bean shaped object). The protease and tag may also be fused N-terminal to the protein of interest.

In some embodiments, the fusion protein or polypeptide (a TimeSTAMP construct) is substantially purified. By a substantially pure protein or polypeptide is meant a TimeSTAMP polypeptide which has been separated from components which naturally accompany it. Typically, the protein or polypeptide is substantially pure when it is at least 60%, by weight, free from the proteins and naturally-occurring organic molecules with which it is naturally associated. Typically, the preparation is at least 75%, at least 90%, and more typically at least 99%, by weight, of the protein. A substantially pure protein may be obtained, for example, by extraction from a natural source (e.g., a plant cell); by expression of a recombinant nucleic acid encoding a TimeSTAMP polypeptide; or by chemically synthesizing the protein. Purity can be measured by any appropriate method, e.g., column chromatography, polyacrylamide gel electrophoresis, or by HPLC analysis.

A protein or polypeptide is substantially free of naturally associated components when it is separated from those contaminants which accompany it in its natural state. Thus, a protein or polypeptide which is chemically synthesized or produced in a cellular system different from the cell from which it naturally originates will be substantially free from its naturally associated components. Accordingly, substantially pure polypeptides include those derived from eukaryotic organisms but synthesized in E. coli or other prokaryotes.

A TimeSTAMP polypeptide can also include a targeting sequence to direct the TimeSTAMP polypeptide to particular cellular sites by fusion to appropriate organellar targeting signals or localized host proteins. A polynucleotide encoding a targeting sequence can be ligated to the 5' terminus of a polynucleotide encoding the TimeSTAMP polypeptide such that the targeting peptide is located at the amino terminal end of the resulting fusion polynucleotide/polypeptide. The targeting sequence can be, e.g., a signal peptide. In the case of eukaryotes, the signal peptide is believed to function to transport the TimeSTAMP polypeptide across the endoplasmic reticulum. The secretory protein is then transported through the Golgi apparatus, into secretory vesicles and into the extracellular space or, preferably, the external environment. Signal peptides which can be utilized according to the disclosure include pre-pro peptides which contain a proteolytic enzyme recognition site. Other signal peptides with similar properties are known to those skilled in the art, or can be readily ascertained using well known and routine methods.

FIG. 1D demonstrate examples of the disclosure. The C-terminal fusion to the protein Arc(A) and N-terminal fusion to the protein CaMKII-alpha (B) are shown in FIG. 1C-D. Immunoblots were performed to detect preserved tag (top blots) or all protein (lower blots). In each case, two versions of the protease, one more active (left two lanes) and another less active (right two lanes) were used, and proteins were expressed in the absence or presence of the drug BILN-2061, which inhibits removal of the tag by the protease. The amounts of each species (1-4) seen are determined by the relative speed and ability to inhibit each cleavage step.

In another embodiment, the disclosure provides isolated polynucleotides that encode a TimeSTAMP cassette. In one aspect, a polynucleotide encoding a TimeSTAMP Cassette comprises a multiple cloning site for cloning a coding sequence of interest, a nucleic acid encoding a first linker moiety, a nucleic acid encoding a cleavage agent (e.g., a protease), a nucleic acid encoding a second linker moiety and a nucleic acid encoding a detectable tag moiety. In another aspect, a polynucleotide encoding a TimeSTAMP comprises a nucleic acid encoding a polypeptide or protein of interest, a nucleic acid encoding a first linker moiety, a nucleic acid encoding a cleavage agent (e.g., a protease), a nucleic acid encoding a second linker moiety and a nucleic acid encoding a detectable tag moiety. In one aspect, the first and second linker moieties comprise cleavable linker peptides. In another aspect, the first or second linker moiety comprises a cleavable linker peptide. In yet a further aspect, the first and second linker moieties are the same or are different. In one aspect, a polynucleotide of the disclosure encodes distinct peptide and polypeptide domains as a single fusion construction, wherein each domain is functionally operative.

The term "polynucleotide" or "nucleic acid" refers to a polymeric form of nucleotides. By "isolated polynucleotide" is meant a polynucleotide that is no longer immediately contiguous with both of the coding sequences with which it was immediately contiguous (one on the 5' end and one on the 3' end) in the naturally occurring genome of the organism from which it is derived. As such, the term "isolated polynucleotide" includes, for example, a recombinant DNA, which can be incorporated into a vector, including an autonomously replicating plasmid or virus; or into the genomic DNA of a prokaryotic or eukaryotic cell or organism; or that exists as a separate molecule (e.g. a cDNA) independent of other sequences. The nucleotides of the disclosure can be ribonucleotides, deoxyribonucleotides, or modified forms thereof, and the polynucleotides can be single stranded or double stranded.

The term "operatively linked" refers to a juxtaposition wherein the components so described are in a relationship permitting them to function in their intended manner. With reference to nucleic acids that are operatively linked, each distinct nucleic acid molecule is ligated in such a way so as to encode a polypeptide that is functional for its intended purpose. For example, an expression control sequence operatively linked to a coding sequence is ligated such that expression of the coding sequence is achieved under conditions compatible with the expression control sequences.

As used herein, the term "expression control element" refers to a nucleic acid that regulates the expression of a polynucleotide to which it is operatively linked. Expression control elements are operatively linked to a nucleic acid when the expression control elements control and regulate the transcription and, as appropriate, translation of the nucleic acid. Thus, expression control elements can include appropriate promoters, enhancers, transcription terminators, a start codon (i.e., ATG) in front of a protein-encoding nucleic acid sequence, splicing signals for introns, maintenance of the correct reading frame of that gene to permit proper translation of the mRNA, and stop codons. The term "control domain" is intended to include, at a minimum, components whose presence can influence expression, and can also include additional components whose presence is advantageous, for example, leader sequences and chimeric partner sequences.

The term "promoter" refers to a minimal sequence sufficient to direct transcription. Also included in the disclosure are those promoter elements that are sufficient to render promoter-dependent gene expression controllable for cell-type specific, tissue-specific, or inducible by external signals or agents; such elements may be located in the 5' or 3' regions of the gene. Both constitutive and inducible promoters, are included in the disclosure (see e.g., Bitter et al., 1987, Methods in Enzymology 153:516 544). For example, when cloning in bacterial systems, inducible promoters such as pL of bacteriophage-gamma, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter; CMV promoter) may be used. Promoters produced by recombinant DNA or synthetic techniques may also be used to provide for transcription of the nucleic acid sequences of the disclosure.

In the disclosure, polynucleotide encoding the TimeSTAMP or TimeSTAMP cassette of the disclosure may be inserted into a recombinant expression vector. The term "recombinant expression vector" refers to a plasmid, virus or other vehicle known in the art that has been manipulated by insertion or incorporation of the nucleic acid encoding the TimeSTAMP polypeptide of the disclosure. The expression vector typically contains an origin of replication, a promoter, as well as specific genes which allow phenotypic selection of the transformed cells. Vectors suitable for use in the disclosure include, but are not limited to, the T7-based expression vector for expression in bacteria (Rosenberg et al., Gene, 56:125, 1987), the pMSXND expression vector, or adeno or vaccinia viral vectors for expression in mammalian cells (Lee and Nathans, J. Biol. Chem., 263:3521, 1988), baculovirus-derived vectors for expression in insect cells, cauliflower mosaic virus, CaMV; tobacco mosaic virus, TMV.

The polynucleotide encoding a TimeSTAMP of the disclosure can also include a localization sequence to direct the TimeSTAMP polypeptide to particular cellular sites by fusion to appropriate organellar targeting signals or localized host proteins. A polynucleotide encoding a localization sequence, or signal sequence, can be ligated or fused at the 5' terminus of a polynucleotide encoding the TimeSTAMP polypeptide such that the signal peptide is located at the amino terminal end of the resulting chimeric polynucleotide/polypeptide. In the case of eukaryotes, the signal peptide is believed to function to transport the chimeric polypeptide across the endoplasmic reticulum. The secretory protein is then transported through the Golgi apparatus, into secretory vesicles and into the extracellular space or, preferably, the external environment. Signal peptides that can be utilized according to the disclosure include pre-propeptides which contain a proteolytic enzyme recognition site. Other signal peptides with similar properties to those described herein are known to those skilled in the art, or can be readily ascertained without undue experimentation.

The localization sequence can be a nuclear localization sequence, an endoplasmic reticulum localization sequence, a peroxisome localization sequence, a mitochondrial localization sequence, or a localized protein. Localization sequences can be targeting sequences which are described, for example, in "Protein Targeting", Chapter 35 of Stryer, Biochemistry (4th ed.), W. H. Freeman, 1995. The localization sequence can also be a localized protein. Some important localization sequences include those targeting the nucleus, mitochondrion, endoplasmic reticulum at C-terminus, (assuming a signal sequence, present at N-terminus), peroxisome, synapses (S/TDV or fusion to GAP 43, kinesin and tau) prenylation or insertion into plasma membrane, cytoplasmic side of plasma membrane (chimeric to SNAP-25), or the Golgi apparatus (chimeric to furin). The construction of expression vectors and the expression of genes in transfected cells involves the use of molecular cloning techniques also well known in the art (see, for example, Sambrook et al., Molecular Cloning: A Laboratory Manual (Cold Spring Harbor Laboratory Press 1989); and Current Protocols in Molecular Biology, Ausubel et al., eds. (Greene Publishing Associates, Inc., and John Wiley & Sons, Inc., 1994, and most recent Supplement). These methods include in vitro recombinant DNA techniques, synthetic techniques and in vivo recombination/genetic recombination. (See, for example, Sambrook et al., supra, 1989).

Depending on the vector utilized, any of a number of suitable transcription and translation elements, including constitutive and inducible promoters, transcription enhancer elements, transcription terminators, etc. may be used in the expression vector (see, e.g., Bitter, et al., Meth. Enzymol. 153:516 544, 1987). Such elements are well known in the art.

In bacterial systems a number of expression vectors may be advantageously selected depending upon the intended use. For example, when large quantities of a protein of the disclosure is desired, vectors which direct the expression of high levels of chimeric protein products that are readily purified may be desirable. Those which are engineered to contain a cleavage site to aid in protein recovery are useful.

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., Expression and Secretion Vectors for Yeast, in Meth. Enzymol., Eds. Wu & Grossman, 31987, Academic Press NY, Vol. 153, pp. 516 544, 1987; Glover, DNA Cloning, Vol. II, IRL Press, Wash., D.C., Ch. 3, 1986; and Bitter, Heterologous Gene Expression in Yeast, Methods in Enzymology, Eds. Berger & Kimmel, Acad. Press, N.Y, Vol. 152, pp. 673 684, 1987; and The Molecular Biology of the Yeast Saccharomyces, Eds. Strathern et al., Cold Spring Harbor Press, Vols. I and II, 1982. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. D M Glover, IRL Press, Wash., D.C., 1986). Alternatively, vectors may be used which promote integration of foreign DNA sequences into the yeast chromosome.

An alternative expression system which could be used to express the polypeptides of the disclosure is an insect system. In one such system, *Autographa californica* nuclear polyhedrosis virus (AcNPV) is used as a vector to express foreign genes. The virus grows in *Spodoptera frugiperda* cells. The sequence encoding a protein of the disclosure may be cloned into non-essential regions (for example, the polyhedrin gene) of the virus and placed under control of an AcNPV promoter (for example the polyhedrin promoter). Successful insertion of the sequences coding for a protein of the disclosure will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed, see Smith et al., J. Virol. 46:584, 1983; Smith, U.S. Pat. No. 4,215,051. Another alternative expression system includes plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a TimeS-TAMP.

By "transformation" is meant a permanent or transient genetic change induced in a cell following incorporation of new DNA (i.e. DNA exogenous to the cell). Where the cell is a mammalian cell, a permanent genetic change is generally achieved by introduction of the DNA into the genome of the cell.

By "transformed cell" is meant a cell into which (or into an ancestor of which has been introduced), by means of recombinant DNA techniques, a DNA molecule encoding a TimeS-TAMP.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the CaCl2 method by procedures well known in the art. Alternatively, MgCl2 or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the chimeric polypeptide of the disclosure, and a second foreign DNA molecule encoding a selectable phenotype, such as the herpes simplex thymidine kinase gene. Another method is to use a eukaryotic viral vector, such as simian virus 40 (SV40) adenovirus, vaccinia virus, or bovine papilloma virus, to transiently infect or transform eukaryotic cells and express the protein. (Eukaryotic Viral Vectors, Cold Spring Harbor Laboratory, Gluzman ed., 1982). Preferably, a eukaryotic host is utilized as the host cell as described herein. Methods of stable transfer, meaning that the foreign DNA is continuously maintained in the host, are known in the art.

Eukaryotic systems, and mammalian expression systems, allow for proper post-translational modifications of expressed mammalian proteins to occur. Eukaryotic cells which possess the cellular machinery for proper processing of the primary transcript, glycosylation, phosphorylation, and, secretion of the gene product should be used as host cells for the expression of fluorescent indicator. Such host cell lines may include but are not limited to CHO, VERO, BHK, HeLa, COS, MDCK, Jurkat, HEK-293, and WI38.

Mammalian cell systems which utilize recombinant viruses or viral elements to direct expression may be engineered. For example, when using adenovirus expression vectors, the nucleic acid sequences encoding a TimeSTAMP of the disclosure may be ligated to an adenovirus transcription/translation control complex, e.g., the late promoter and tripartite leader sequence. This nucleic acid sequence may then be inserted in the adenovirus genome by in vitro or in vivo recombination. Insertion in a non-essential region of the viral genome (e.g., region E1 or E3) will result in a recombinant virus that is viable and capable of expressing the fluorescent indicator in infected hosts (see, for example, Logan & Shenk, Proc. Natl. Acad. Sci. USA, 81: 3655 3659, 1984). Alternatively, the vaccinia virus 7.5K promoter may be used (see, for example, Mackett et al., Proc. Natl. Acad. Sci. USA, 79: 7415 7419, 1982; Mackett et al., J. Virol. 49: 857 864, 1984; Panicali et al., Proc. Natl. Acad. Sci. USA 79: 4927 4931, 1982). Of particular interest are vectors based on bovine papilloma virus which have the ability to replicate as extrachromosomal elements (Sarver et al., Mol. Cell. Biol. 1: 486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the TimeSTAMP polypeptide in host cells (Cone and Mulligan, Proc. Natl. Acad. Sci. USA, 81:6349 6353, 1984). High level expression may also be achieved using inducible promoters, including, but not limited to, the metallothionein IIA promoter and heat shock promoters.

For long term, high yield production of recombinant proteins, stable expression can be used. Rather than using expression vectors which contain viral origins of replication, host cells can be transformed with the cDNA encoding a TimeSTAMP of the disclosure controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in an enriched media, and then are switched to a selective media. A number of selection systems may be used including, but not limited to, the herpes simplex virus thymidine kinase (Wigler et al., Cell, 11: 223, 1977), hypoxanthine-guanine phosphoribosyltransferase (Szybalska and Szybalski, Proc. Natl. Acad. Sci. USA, 48:2026, 1962), and adenine phosphoribosyltransferase (Lowy et al., Cell, 22: 817, 1980) genes can be employed in tk−, hgprt− or aprt− cells respectively. Also, antimetabolite resistance can be used as the basis of selection for dhfr, which confers resistance to methotrexate (Wigler et al., Proc. Natl. Acad. Sci. USA, 77: 3567, 1980; O'Hare et al., Proc. Natl. Acad. Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin et al., J. Mol. Biol., 150:1, 1981); and hygro, which confers resistance to hygromycin (Santerre et al., Gene, 30: 147, 1984) genes. Recently, additional selectable genes have been described, namely trpB, which allows cells to utilize indole in place of tryptophan; hisD, which allows cells to utilize histinol in place of histidine (Hartman and Mulligan, Proc. Natl. Acad. Sci. USA, 85:8047, 1988); and ODC (ornithine decarboxylase) which confers resistance to the ornithine decarboxylase inhibitor, 2-(difluoromethyl)-DL-ornithine, DFMO (McConlogue, In: Current Communications in Molecular Biology, Cold Spring Harbor Laboratory, ed., 1987).

A TimeSTAMP of the disclosure can be produced by expression of a polynucleotide encoding a TimeSTAMP polypeptide in prokaryotes. These include but are not limited to microorganisms such as bacteria transformed with recombinant bacteriophage DNA, plasmid DNA or cosmid DNA expression vectors encoding a TimeSTAMP of the disclosure. A advantage of the polypeptides of the disclosure is that they are prepared by normal protein biosynthesis, thus avoiding organic synthesis and the requirement for customized unnatural amino acid analogs. The constructs can be expressed in *E. coli* in large scale for in vitro assays. Purification from bacteria is simplified when the sequences include tags for one-step purification by nickel-chelate chromatography. The construct can also contain a domain to simplify isolation of the fluorescent indicator. For example, a polyhistidine domain of, e.g., six histidine residues, can be incorporated at the amino terminal end of the TimeSTAMP polypeptide. The polyhistidine domain allows convenient isolation of the protein in a single step by nickel-chelate chromatography. Alternatively, the substrates can be expressed directly in a desired host cell for assays in situ.

Techniques for the isolation and purification of either microbially or eukaryotically expressed polypeptides of the disclosure may be by any conventional means such as, for example, preparative chromatographic separations and immunological separations such as those involving the use of monoclonal or polyclonal antibodies or antigen.

In another embodiment, the disclosure features a method for determining protein turnover/age of a protein in a cell comprising transfecting the cell with a nucleic acid encoding a TimeSTAMP of the disclosure; measuring the tag; contacting with an inhibitor; and measuring the amount of tag, such that a change in the tag measurement is indicative of a change in protein.

The disclosure additionally, features methods for determining transient changes in a chemical, biological, electrical or physiological parameter, by contacting the sample with a TimeSTAMP of the disclosure and measuring a change in the tag property over time.

It is understood that the cell containing a nucleic acid sequence encoding a TimeSTAMP of the disclosure can be used to co-transfect other genes of interest in order to determine the effect of the gene product of that gene on the cell comprising the TimeSTAMP. Therefore, a cell containing such a nucleic acid is a composition provided by the disclosure.

An advantage of the disclosure is that it is compatible with the wide array of methods for detecting polypeptides and peptides, such as immunoblotting, immunocytochemistry, binding of compounds that recognize specific peptide sequence (including biarsenical compounds or alpha bungarotoxin), or enzymatic modification of specific peptide sequences (such as biotinylation by biotin ligase). In particular, immunocytochemistry can allow for very sensitive detection of proteins at levels lower than total endogenous levels.

Second, as a method for controlling protein expression, there is currently no generalizable method that allows rapid drug-induced inhibition of protein function in a single-protein system. For example, current methods for shutting down protein expression involve regulation at the transcriptional level or drug-induced heterodimerization of the protein of interest with a second introduced regulatory protein. The single component system will respond more rapidly and robustly than systems dependent on altering transcription or intermolecular interactions.

Third, no known system allows for rapid drug-controlled targeting or proteins to subcellular structures. This could be useful, for example, in rapidly inducing the localization of transcription factors to the nucleus or cell death proteins to mitochondria, where they exert their functions respectively. Existing technologies utilizing transcriptional induction, on the other hand, require about 24 hours for induction.

The disclosure can be used in research requiring the detection of newly synthesized proteins from transgenes. For example, the new synthesis of certain proteins correlates with neuronal activation, and so tracking new synthesis may be of interest for companies performing research in neurobiology, stem cells for neural repair, and track the appearance of synaptic proteins during stem cell differentiation. In addition, the disclosure an also be used to target proteins expressed in gene therapy to subcellular structure or to the degradation machinery in a drug inducible manner.

The disclosure can be used in screening assays to determine whether a compound (e.g., a drug, a chemical or a biologic) alters the activity of a particular protein, i.e., the TimeSTAMP polypeptide. In one embodiment, the assay is performed on a sample containing the TimeSTAMP polypeptide in vitro. A sample comprising a TimeSTAMP polypeptide is mixed with the co-factors required for activity, and with a test compound. The amount of the tag in the sample is then determined by measuring a tag property, such as a fluorescent property, at least a first and second time after contact between the sample, the TimeSTAMP polypeptide of the disclosure, and any co-factors or components required to conduct the reaction, and the test compound. Then the amount of tag or tag property, for example, in the presence of the test compound is compared with the amount of tag or a tag property in the absence of the test compound. A difference indicates that the test compound alters the activity of the polypeptide.

The materials of the disclosure are ideally suited for a kit. Such a kit may contain a container containing a TimeSTAMP polypeptide or fragment thereof. In another embodiment, a kit of the disclosure contains an isolated nucleic acid which encodes a TimeSTAMP polypeptide The nucleic acid of the kit may be contained in a host cell, either stably transfected or transiently transfected.

The disclosure provides a TimeSTAMP composition, methods and system for a drug-mediated epitope tagging of newly synthesized proteins. The compositions and methods of the disclosure allow sensitive and specific detection of newly synthesized proteins of interest in a manner that is non-perturbing, non-toxic, and generalizable. Taking advantage of these attributes the Examples below demonstrate the ability of composition of the disclosure to observe synthesized copies of the synaptic protein PSD-95 in neurons over time intervals of several hours, and have demonstrated that growing synapses preferentially accumulate new proteins. In addition, the Examples below demonstrate that the compositions can be used to visualize the distribution of newly synthesized dCaMKII throughout the brain of Drosphila, demonstrating that the composition can be used in freely behaving animals.

TimeSTAMP uniquely combines the temporal resolution and tissue penetrance of small-molecule regulation and the high spatial resolution and sensitivity of antibody-based detection. The ability of TimeSTAMP to be regulated by cell permeable drugs makes it well suited for situations where optical access is difficult, e.g. tissue explants or living animals. The sensitivity of immunocytochemistry, where signal amplification can be achieved with secondary antibodies, can be especially advantageous in the visualization of low-abundance proteins. For example, synaptic proteins such as PSD-95 are present at a few hundred copies per synapse (Chen et al., 2005; Sugiyama et al., 2005), only a fraction of which will be synthesized within a few hours. In contrast, the application of photoconvertible proteins is hampered by the inability to further amplify the signal, background from non-converted protein, and photobleaching of converted protein. Similarly, TimeSTAMP would be suitable for studying protein trafficking in secretory pathways at physiological levels of protein expression, when only a few copies of a protein of interest may be present in a secretory vesicle. The utility of TimeSTAMP is demonstrated in immunoblotting, where it allows straightforward quantitation of proteins produced before vs. after a time of interest. TimeSTAMP is complementary to approaches that identify new proteins through incorporation of radioactive amino acids or unnatural analogs (Dieterich et al., 2006). In some aspect, these approaches do not require selection of candidate proteins for tagging but may be dominated by abundant high-turnover proteins, and therefore are typically coupled to additional protein purification methods such as mass spectroscopy (Dieterich et al., 2007) at the cost of spatial resolution. TimeSTAMP is therefore uniquely suited for applications where newly synthesized copies of specific proteins need to be labelled for investigating spatial relationships or for quantifying rates of protein production in genetically labelled cellular populations in vitro or in vivo.

The TimeSTAMP strategy is easily adaptable to other antibody-based detection methods. For example, immuno-electron microscopy on TimeSTAMP-tagged proteins can be performed to reveal the location of newly synthesized proteins at the synapse with ultrastructural resolution. The TimeSTAMP method also easily lends itself to multiplexing; multiple proteins of interest can be expressed simultaneously as fusions to TimeSTAMP modules containing various epitope tags, which will be individually detected with specific antibodies conjugated to different organic fluorophores for immunofluorescence microscopy or to differently sized quantum dots for correlated immunofluorescence and electron microscopy (Giepmans et al., 2005). Highly specific protease-inhibitor pairs could be used to regulate the persistence on proteins of functional peptide motifs, not just epitope tags.

The results presented herein also provide an approach to identifying synapses undergoing growth within the intact brain in response to environmental changes, learning, or pathway stimulation. Both postsynaptic and presynaptic proteins can be analyzed.

The following non-limiting examples illustrate the various embodiments of the disclosure. Those skilled in the art will recognize many variations that are within the spirit of the disclosure and scope of the claims.

EXAMPLES

DNA Reagents

The NS3-NS4 coding region from HCV genotype 1a strain H77c was obtained by RT-PCR from infected monkey liver RNA. Mouse PSD-95 alpha isoform, mouse Neuroligin, and mouse Arc DNAs were obtained from public library collections. Mammalian expression plasmids were constructed in a pCMVSport6 backbone and fly transformation plasmids were constructed in a pUAST backbone using standard methods and verified by sequencing.

Antibodies.

Primary antibodies used were mouse monoclonal anti-PSD-95 (Neuromab), rat monoclonal anti-HA (Roche), mouse monoclonal anti-T7 (Novagen), and mouse monoclonal anti-HSV (Novagen). Secondary antibodies were HRP-conjugated goat anti-mouse and anti-rat (Zymed) for immunoblotting, and Alexa Fluor 555 anti-rat and highly cross-absorbed Alexa Fluor 647 anti-mouse (Invitrogen) for immunofluorescence. All antibodies were used for immunoblotting at 0.1 mg/L and for immunofluorescence at 0.5-1 mg/L. Specificity of secondaries in immunofluorescence was confirmed in control experiments without primary antibody.

Construction and Testing of TimeSTAMP.

For testing of the drug-regulatable epitope tag concept by immunoblotting, a construct of linear fusions of PSD-95, HCV NS3 protease flanked on both sides by cleavage sites, an HA epitope tag, and the cyan fluorescent protein (CFP) was used. Some fusions, similar to the final TimeSTAMP cassettes, used a NS3 protease domain without the NS3 helicase domain and without the NS4A beta strand, which enhances NS3 protease activity in trans (Wang et al., 2004). For comparison, constructs were tested with a NS3 protease holoenzyme that included the NS4A beta strand N-terminal to the NS3 protease domain, a configuration shown previously to possess high catalytic activity (Lai et al., 2000; Pasquo et al., 1998). In some constructs and in the final TimeSTAMPa cassette, a mutation of Thr-54 to Ala (T54A) was introduced that has been previously shown to reduce the catalytic rate of the enzyme 10-fold (Tong et al., 2006). Analysis of the protease structure (Yao et al., 1997) revealed Thr-54 to be distant from the catalytic triad and the BILN-2061 binding site. Rather, Thr-54 may have a subtle function in positioning the oxyanion hole; a hydrogen bond with the backbone oxygen of Leu-44 may help orient the Leu-44 side chain to interact with the polypeptide backbone of the oxyanion hole.

For cleavage sites, the NS4A/4B junction was chosen, because it is efficiently recognized and cleaved by the NS3 protease and because the NS4A C-terminal sequence following cleavage can bind to the active site and serve as a competitive inhibitor of the protease with an inhibitory constant of 0.6 µM (Steinkuhler et al., 1998), possibly limiting further protease activity. Fusions using cleavage sites from the NS5A/5B junction showed reduced sensitivity to inhibition by BILN-2061, consistent with the faster activity of NS3 protease on this sequence (Tsantrizos et al., 2003). A constructs without a cleavage site in between PSD-95 and the protease domain was also used for comparison purposes.

For each construct, HEK293 cells were transfected with Lipofectamine 2000, grown with or without the NS3 protease inhibitor BILN-2061 (Lamarre et al., 2003), and immunoblotted after boiling/SDS lysis with anti-PSD-95 to differentiate uncleaved and cleaved products by molecular weight. An efficient removal of CFP from the fusion protein was observed in all constructs. Cleavage of constructs that contained the NS3 domain alone without the NS4A cofactor was inhibited by BILN-2061. Inhibition was more complete for NS3 protease domains containing T54A. The construct containing a holoenzyme with a NS4A beta strand and lacking a cleavage site between PSD-95 and the protease showed a detectable amount of off-target cleavage. For immunocytochemistry, a TimeSTAMP cassettes without CFP comprising a NS4A/4B cleavage site, the NS3 domain with either Thr-54 or Ala-54 but lacking the NS4A cofactor, another NS4A/4B cleavage site, and a short HA epitope tag was created and used.

Neuronal Experiments.

Hippocampal neurons were dissected from postnatal day 0 or 1 rat pups and cultured in Neurobasal medium supplemented with B27 and glutamine. For immunoblotting experiments, neurons were transfected prior to plating using the Amaxa Nucleofector protocol. For other experiments, neurons were transfected at 7-10 DIV by calcium phosphate.

For timelapse imaging, 14-21 day in vitro (DIV) neurons with pyramidal morphology expressing dim GFP fluorescence were used. These were imaged for GFP by epifluorescence on a Zeiss Axiovert 200M with a temperature control chamber at 37° C. and a 100× oil objective in HBSS supplemented with B27 and 10 µM BILN-2061. For each position and time point, a stack of 20 images spaced 0.5 µm apart through the neurons was acquired. After fixation with 4% paraformaldehyde for 10 minutes, neurons were stained for HA and synapsin by standard protocols, then imaged again for GFP, HA, and synapsin. Image stacks were cropped to remove sections lost to focal drift and flattened into single maximum projection images for analysis.

For synaptic density quantification in neurons transfected with various fusions of PSD-95-GFP to NS3, maximum intensity projections of stacks of 20 images spaced 0.5 µm apart of 14 DIV neurons at 7 DPT were acquired of GFP fluorescence and synapsin immunofluorescence in a blinded manner. In ImageJ software, a 60 µm-long segment of the primary dendrite beginning 30 µm from the cell body was traced in the GFP channel, then dilated by 1 µm and used as a positive mask for the synapsin channel. Synapsin staining within the mask was isolated using the automatic threshold function. Synaptic density was defined as the area covered by synapsin staining, as calculated using the analyze particles function, divided by the mask area.

For EosFP photoconversion experiments, because photoconversion is most effective at pH <7, neurons expressing proteins fused to tdEosFP were moved into HBSS pH 6.9 supplemented with B27 as a source of antioxidants. Focal photoconversion was performed in a temperature control chamber at 37° C. on an inverted microscope using illumination from a xenon arc lamp passing through a 420/20 nm bandpass filter, a stopped-down diaphragm, and a 100× oil objective. Under these conditions, red fluorescence increases to 4-fold over beginning levels by 1.5 minutes of illumination, remains constant over the next 1.5 minutes, then falls, presumably due to photobleaching. After undergoing rapid and variable photoactivation, green fluorescence drops to 0.5× of maximal values by 1.5 minutes, then to 0.35× by 3 minutes. Further illumination was associated with blebbing of illuminated neurites. To minimize phototoxicity and maximize red fluorescence marking locally converted protein, photoconversion was performed for 3 minutes. Global photoconversion was performed on a solar simulator with a xenon arc lamp passing through a 420/40 bandpass filter for 40 minutes, resulting in a 9-fold increase in red fluorescence and a final green fluorescence 10% of beginning values. After photoconversion, neurons were returned to conditioned Neurobasal with B27 and maintained at 37° C. and 5% $CO_2$, and imaged in HBSS at various times afterwards.

Fly Experiments.

Homozyous transformed lines were established from single progeny of embryos injected with pUAST-HSV-TimeSTAMPt-HA-dCaMKII or pUAST-HSV-TimeS-TAMPa-HA-dCaMKII. Homozygotes showed no behavioral or fertility phenotypes, and no loss of P-elements or transposition to other chromosomes were observed in balanced lines. Homozygous adults had smooth eyes and brains were normal in size. Male homozygotes with third-chromosome insertions were crossed to elav-GAL4; UAS-tubulin-GFP; + females, and the male elavGAL4/Y; UAS-tubulin-GFP/+; HSV-TimeSTAMP-HA-dCaMKII/+ progeny were used for experiments within 2 days post-eclosion.

For experiments involving HSV-TimeSTAMPt-HA-dCaMKII, flies were anesthesized by carbon dioxide, then a hole was punctured in the medial ocellus region using a glass micropipette with a 10 µm bore and a 25 nL drop of 2 mM BILN-2061 in 20% DMSO 5% Cremophor EL in Hank's buffered saline solution (HBSS) was placed over the region. The drug solution was observed to be absorbed within 2 minutes, then flies were returned to food vials with a wetted plug and allowed to recover. Following recovery, flies were observed to feed, fly, and engage in courtship behavior. For HSV-TimeSTAMPa-HA-dCaMKII, flies were starved for 12 hours with only water, then placed in a vial with an emulsion of 30% (w/v) yeast, 30% (v/v) glycerol, 30% (v/v) water, 5% green food coloring, 5% dimethylformamide, and 500 µM BILN-2061. Most flies were observed to ingest the food coloring within 15 minutes. For analysis, flies were decapitated and brains were simultaneously dissected and fixed in HBSS with 4% paraformaldehyde and 0.2% Triton X-100 for 40 minutes at room temperature. Brains were processed for immunocytochemistry by standard methods and imaged on a Zeiss LSM510 or LSM5Live confocal microscope.

Design of a Drug-Regulatable Epitope Tag.

The hepatitis C virus (HCV) NS3 protease was used as uniquely suitable for several reasons: HCV NS3 protease is monomeric, demonstrates an unusual but well characterized substrate specificity, can be expressed in mammalian cells without noticeable toxicity, has been extensively studied biochemically, and can be specifically blocked by cell-permeant drugs developed by the pharmaceutical industry such as BILN-2061 (Bartenschlager, 1999; Thomson and Perni, 2006).

Figure 6A:
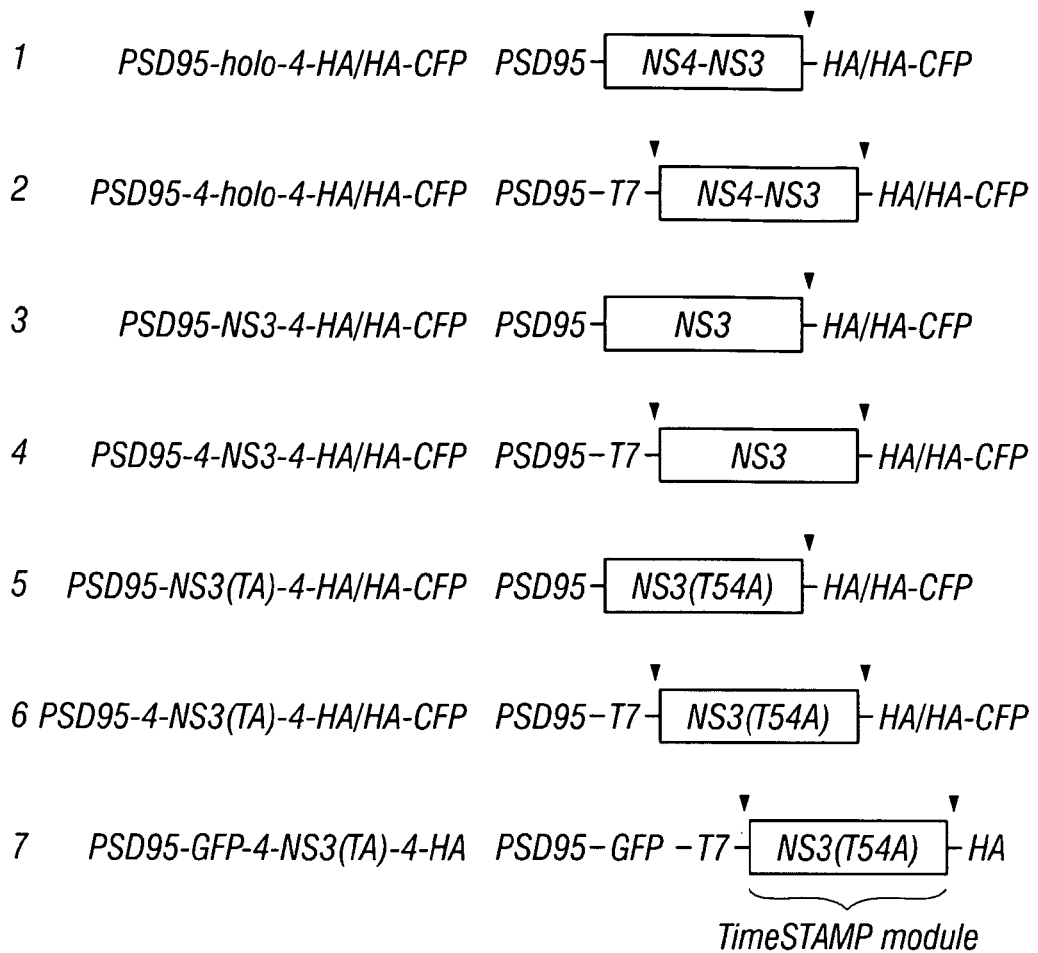
FIG. 6A-D shows additional configurations and data for embodiments of TimeSTAMP. (A) Organization of fusion proteins used. (B) CFP-containing constructs numbers 1-5 from panel (A) were expressed in HEK293 cells in 0, 1 µM, or 10 µM BILN-2061 and cleavage of the constructs assayed by immunoblotting. (C) The T54A reduced activity mutation is unlikely to affect substrate or BILN-2061 binding. Substrate-bound NS3 was rendered based on coordinates from PDB accession 1CU1. A P1 to P6 substrate is shown as light shaded sticks. The BILN-2061 contact surface, the catalytic triad, and the oxyanion hole are depicted. The backbone atoms of the oxyanion hole residues are shown as dark sticks. The side chain and backbone carbonyl of leucine 44 and the side chain of threonine 54 are shown as sticks with carbon atoms, oxygen, and hydrogen. (D) The TimeSTAMP module functions at either the N-terminus or C-terminus. HEK293 cells expressing Arc-TimeSTAMPa-HA at 37° C. (left) or HSV-TimeSTAMPt-HA-dCaMKII or HSV-TimeSTAMPa-HA-dCaMKII at 25° C. (right) in the continual absence or presence of BILN-2061 were analyzed by immunoblotting.
Figure 6B:
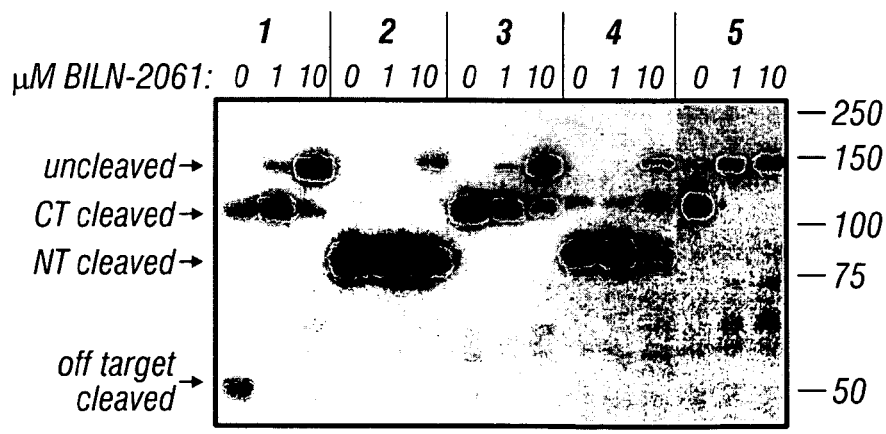
Figure 6C:
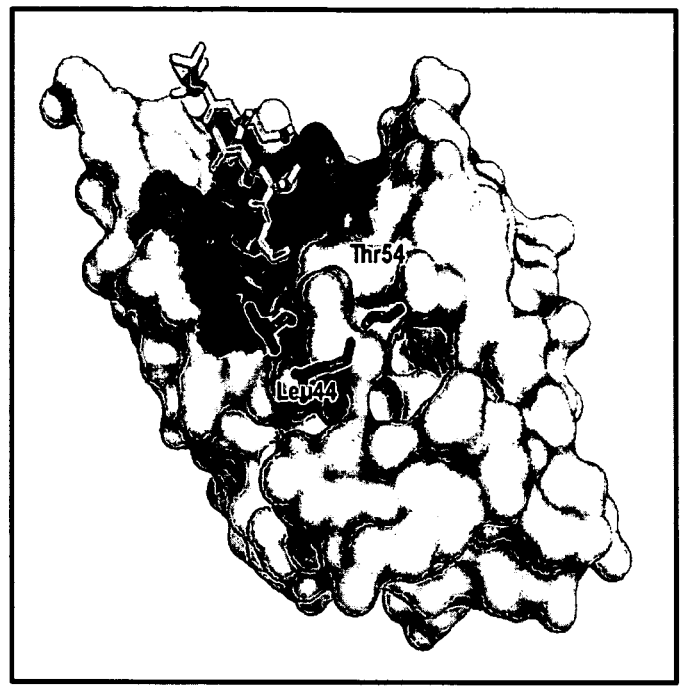
Figure 6D:
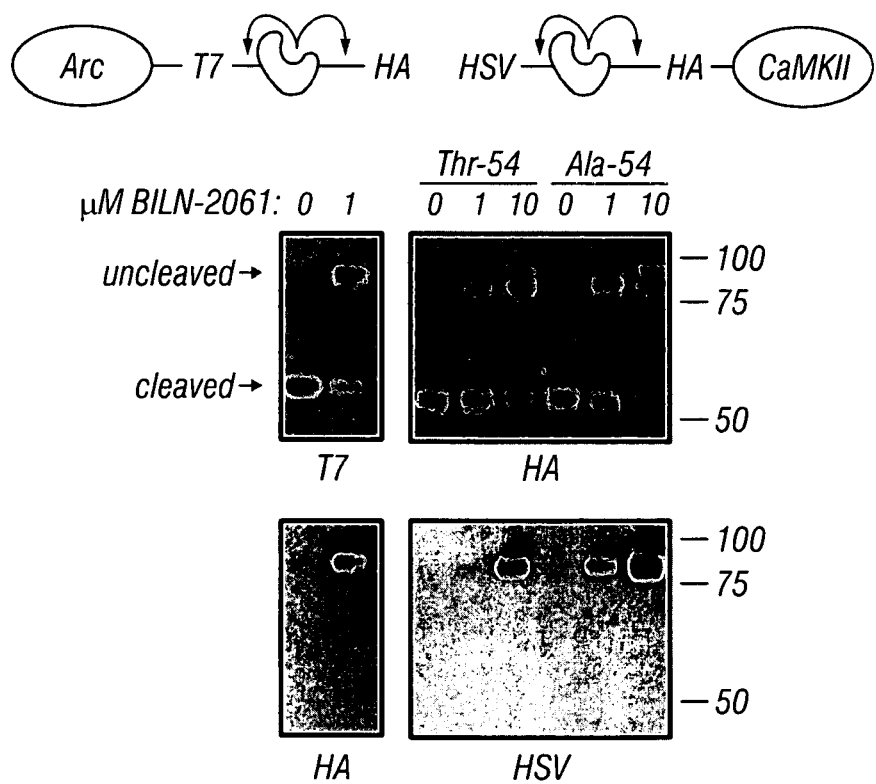

Experiments using the constructs of the disclosure were performed in transiently transfected mammalian cells by immunoblotting. A model protein of interest was fused to various linear combinations of an NS3 protease domain, cognate protease sites, and epitope tags (FIG. 6A,B). An effective combination was an N-terminal epitope tag, a cleavage sequence from the HCV polypeptide NS4A/4B junction, an NS3 protease domain containing a catalysis impairing mutation of Thr-54 to Ala (FIG. 6C), another NS4A/4B cleavage sequence, and a C-terminal epitope tag. This group of elements is referred to as a TimeSTAMP cassette. The NS3 domain and C-terminal epitope tag were efficiently cleaved from PSD-95 in the absence of BILN-2061, and this cleavage was inhibited by BILN-2061 (FIG. 1B). As expected from its symmetric design, the TimeSTAMP cassette mediates drug-dependent tagging at either the C-terminus or the N-terminus of proteins (FIG. 6D). In the case of highly overexpressed proteins, Thr-54 can be restored to the NS3 domain to enhance cleavage if detectable amounts of epitope tag remain in the absence of drug (FIG. 6D). A TimeSTAMP cassette with the less active (Ala-54) form of NS3 as TimeSTAMPa, and with wild-type (Thr-54) NS3 as TimeSTAMPt were developed. No off-target cleavage was observed in various model proteins using either TimeSTAMP cassette (FIG. 1B, FIG. 6D).

TimeSTAMP Labels Newly Synthesized Proteins in Mammalian Cells.

Figure 2A:
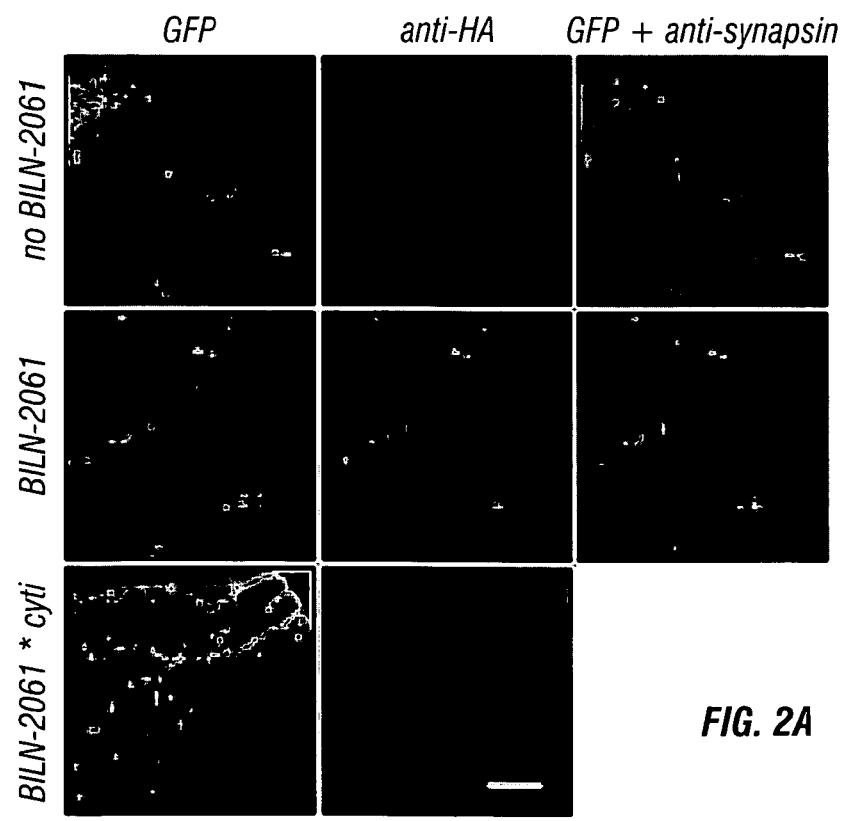
FIG. 2A-E shows exemplary TimeSTAMP implementation and results obtained form such a construct of the disclosure. (A) TimeSTAMP-mediated staining is specific for newly synthesized proteins. 18 day in vitro (DIV) neurons at 9 days post-transfection (DPT) with PSD-95-GFP-TimeSTAMPa-HA show synaptic HA staining after 6 hours of BILN-2061. No staining is seen without BILN-2061 or when protein synthesis is blocked by 50 μg/mL cycloheximide. (B) Quantitative HA immunofluorescence of 18 DIV neurons at 9 DPT shows mean contrast of 121-fold and 20-fold for PSD-95-TimeSTAMPt and PSD-95-TimeSTAMPa respectively, with PSD-95-TimeSTAMP demonstrating higher mean signal levels. Data are represented as mean+/−SEM. (C) To assess limits of detection, 21 DIV neurons at 11 DPT were stained for PSD-95 and HA after 6 hours of BILN-2061. Measurement of maximum PSD-95 immunofluorescence (IF) in untransfected or transfected neurites shows HA staining of sub-endogenous amounts of PSD-95. (D) Basal PSD-95 turnover in 21 DIV neurons at 21 DPT was assayed by quantitative immunoblotting. 22% of total transfected PSD-95 was synthesized in 12 hours. (E) TimeSTAMP reports spatial distributions of new proteins. After 6 hours in BILN-2061, a clear gradient of newly synthesized PSD-95 from the cell soma can be seen. Scale bars, 20 μm. Maximum intensity projections of confocal (A, C) or epifluorescence images (E) spaced 0.5 μm through the neuron are shown.
Figure 2B:
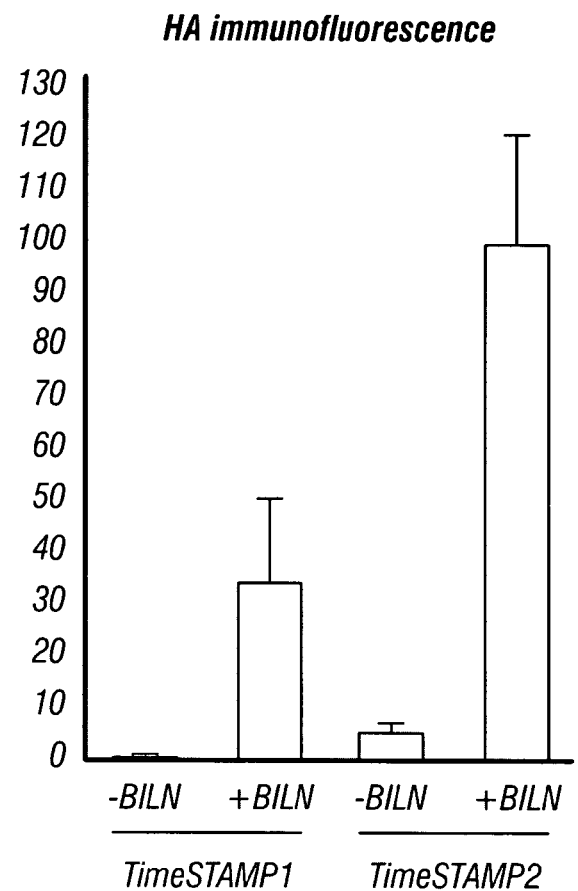
Figure 2C:
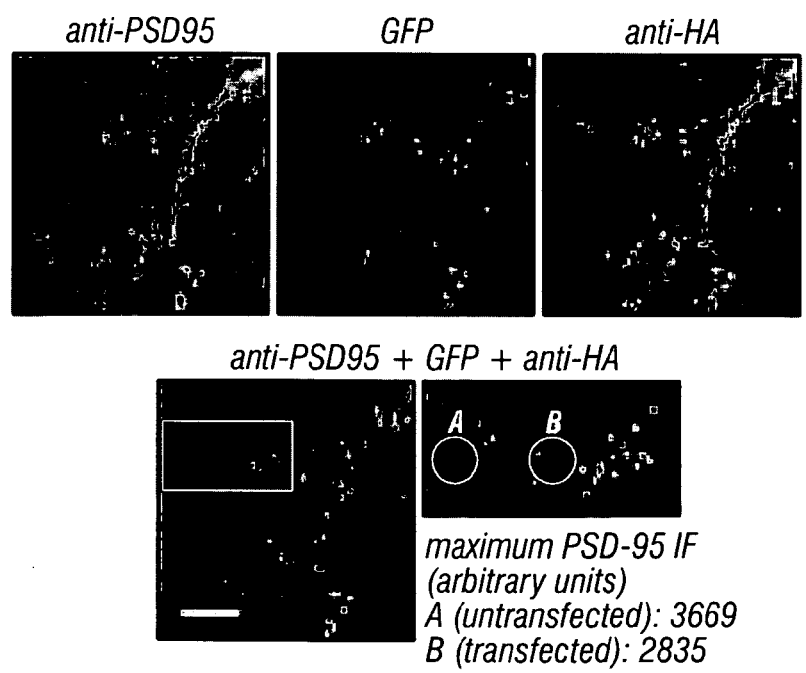
Figure 7A:
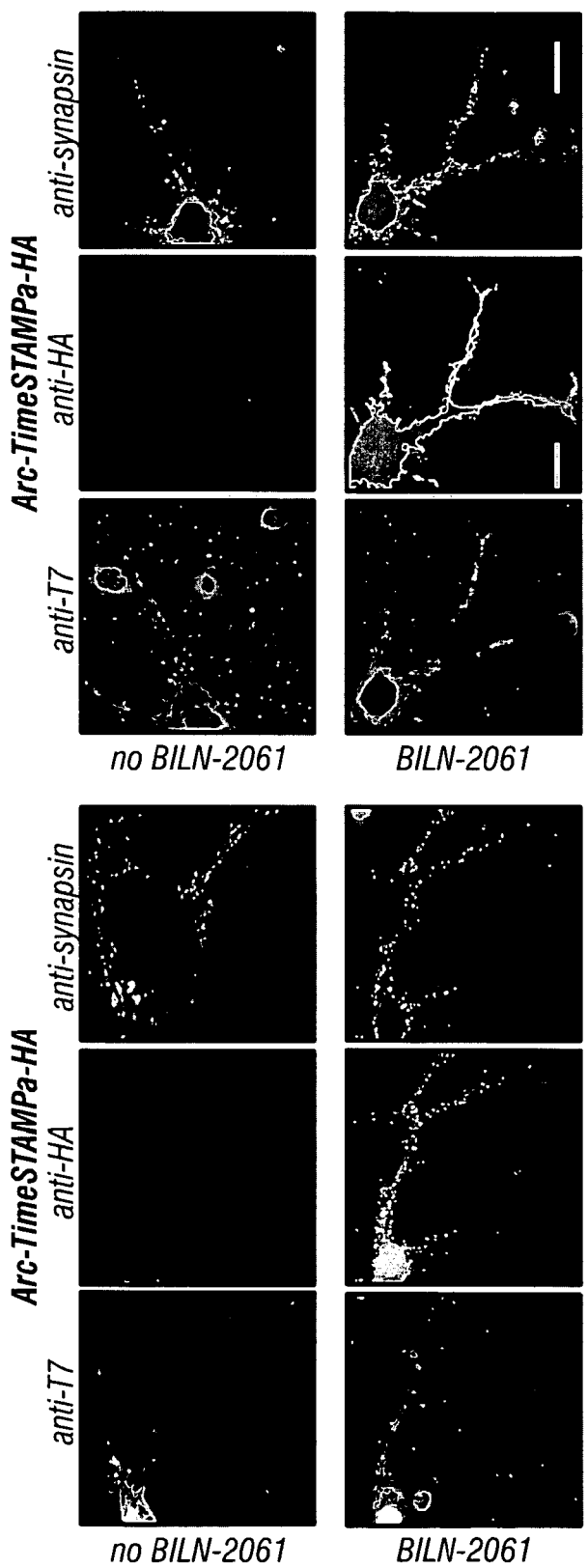
FIG. 7A-D shows that TimeSTAMP is generalizable and functions in neurons without toxicity. (A) Neurons were transfected at 9 DIV with fusion of Arc (left) or Neuroligin1 (Nlg1, right) to TimeSTAMPa-HA and grown in the absence or presence of BILN-2061 for 3 days. To mark synapses, Nlg1-TimeSTAMPa-HA-expressing neurons were cotransfected with PSD-95-GFP and Arc-TimeSTAMPt-HA-expressing neurons were stained for synapsin. T7 is a constitutive tag located N-terminal to the left cleavage site, and HA is drug-dependent. Anti-T7 cross-reactivity to the nucleus has been previously observed in various cell types. (B) TimeSTAMP detects stimulus-dependent new protein synthesis in neurons. Neurons were transfected by Amaxa Nucleofection at 0 DIV with Arc-TimeSTAMPa-HA and analyzed at 7DIV. HA-tagged Arc appearing after incubation in 10 µM BILN for 6 hours was blocked with simultaneous cycloheximide (50 µg/mL) treatment and increased with simultaneous BDNF stimulation. (C) Quantification of synaptic density in cells transfected with the PSD-95 fusions shown in FIG. 6A. Each condition contained 5 neurons scored blinded. Differences were significant by ANOVA (p=0.0057). Only permanent fusions of wild-type NS3 show significantly lower synaptic density in the absence of inhibitor (p<0.05 on pairwise t-tests, asterisks). Data are represented as mean+/−SEM. (D) Nlg1-TimeSTAMPa-HA reveals distribution of newly synthesized Nlg1 after 6 hours. Scale bars, 20 µm.
Figure 7B:
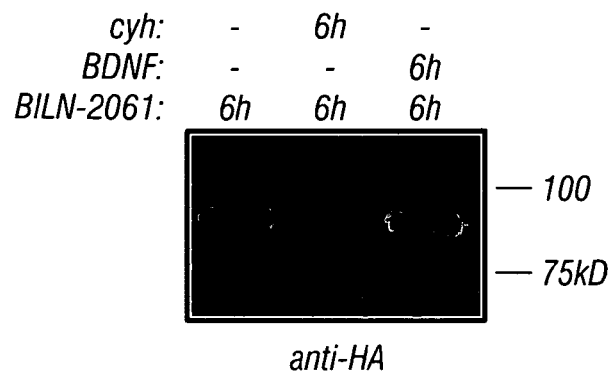

TimeSTAMP was tested for the ability to detect newly synthesized proteins by immunostaining, using as a model system PSD-95 in primary hippocampal neurons, where this protein shows well defined localization in puncta on dendritic spines. Cultured hippocampal neurons expressing PSD-95 fused to GFP and TimeSTAMPa with a C-terminal HA tag (PSD-95-GFP-TimeSTAMPa-HA) showed punctate HA immunofluorescence in the presence of BILN-2061, but not in its absence (FIG. 2A). Similar results were obtained with TimeSTAMPa fusions to two other synaptic proteins, Arc and Neuroligin1 (FIG. 7A). To recapitulate endogenous mechanisms of mRNA localization and translation, the 5' and 3' untranslated regions of each gene were included in all constructs. Tag appearance after BILN-2061 was specific for newly synthesized proteins, as it did not occur in the presence of cycloheximide (FIG. 2A), and in the case of Arc-TimeS-TAMPa-HA, was enhanced during translational induction by growth factor treatment (FIG. 7B). HA immunofluorescence was induced 20-fold by BILN-2061 in the case of TimeS-TAMPa and 121-fold in the case of TimeSTAMPt (FIG. 2B). While TimeSTAMPt-HA conferred lower maximal HA signal in the presence of drug, fold induction was higher due to nearly undetectable signal in the absence of drug (FIG. 2B). The TimeSTAMPa fusion allowed detection of newly synthesized PSD-95-GFP-TimeSTAMPa-HA at levels comparable to endogenous PSD-95 (FIG. 2C). Thus, TimeSTAMP is a generalizable method for drug-controlled visualization of newly synthesized proteins with the ability to detect newly synthesized proteins expressed near endogenous levels.

Figure 2D:
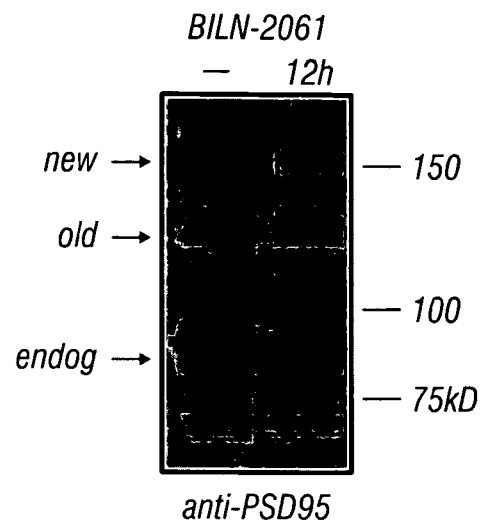
Figure 7C:
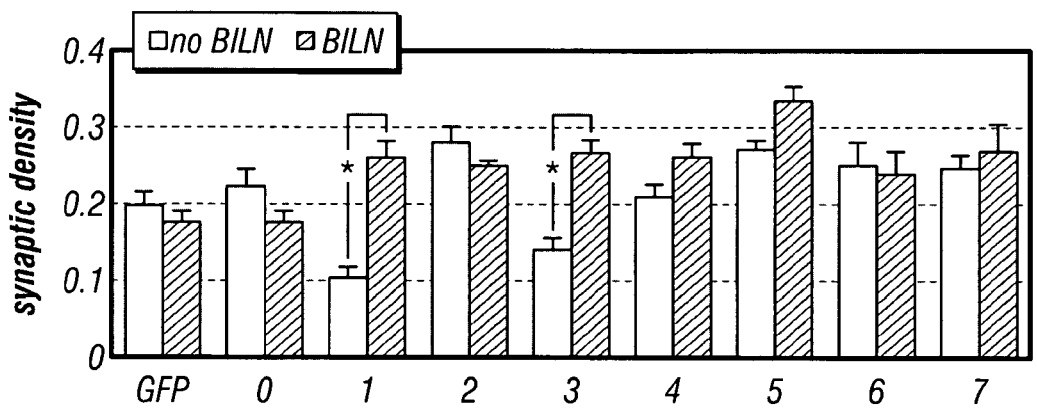

PSD-95-GFP-TimeSTAMPa-HA was present in dendrites and enriched in puncta in dendritic spines, indicating proper localization of the fusion protein (FIG. 2A). TimeSTAMP tagging did not significantly affect protein turnover, as replacement rates of PSD-95-GFP-TimeSTAMPa-HA in stably transfected neurons were consistent with the previously measured 36-hour half-life of endogenous PSD-95 (FIG. 2D) (El-Husseini et al., 2002). No abnormalities in neuronal morphology or synaptic density with PSD-95-TimeSTAMPa-HA expressed throughout synaptogenesis were observed (FIG. 7C). No effect on synaptic density if release of the NS3 protease domain from PSD-95 by abolishing the intervening cleavage site was observed (FIG. 7C), indicating that NS3 activity is insufficient to perturb synaptic development even if concentrated at synapses by fusion to PSD-95. These experiments demonstrate that the TimeSTAMP-mediated staining of newly synthesized proteins is nonpertubative and nontoxic.

Figure 2E:
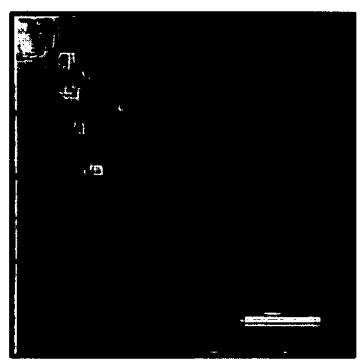
Figure 7D:
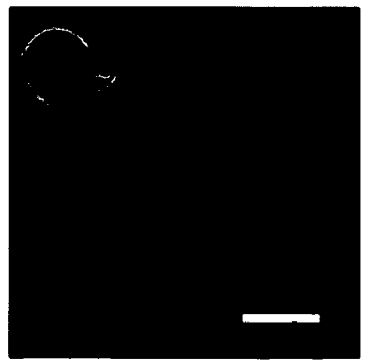

Neurons expressing PSD-95-GFP-TimeSTAMPa-HA were incubated with BILN-2061 for 6 hours, followed by HA staining to detect newly synthesized PSD-95. A gradient of new PSD-95 from the soma along the primary dendritic shaft was observed in most neurons, distinct from total PSD-95 which was distributed throughout the cell (FIG. 2E). Neurons expressing Neuroligin1 fused to TimeSTAMPa-HA were also incubated with BILN-2061 for 6 hours, and new Neuroligin1 protein was observed predominantly in the soma (FIG. 7D), distinct from total Neuroligin1 and likely reflecting slow processing through the secretory pathway. To verify these findings using an independent method, neurons were transfected with PSD-95 or Neuroligin1 fused to tandem dimer EosFP, which irreversibly converts from a green- to a red-emitting fluorescent protein upon near-UV irradiation (Wiedenmann et al., 2004). After photoconversion of existing protein into red fluorescence, newly synthesized protein should appear as green fluorescence. Using this method, newly synthesized PSD-95-tdEosFP was confirmed to exist in a gradient from the soma, and that Neuroligin1 is predominantly localized in the cell body in the first 6 hours after synthesis (FIG. 8A). These results verify that the TimeSTAMP system can report the spatial distribution of newly synthesized proteins.

Application of TimeSTAMP to Tracking Synapse Formation.

Growth or de novo formation of synapses occurs in response to alterations in circuit activity or biochemical stimulation and have been hypothesized to underlie some forms of learning (Kopec et al., 2006; Harris et al., 2003; Matsuzaki et al., 2004; Otmakhov et al., 2004; Nagerl et al., 2004). Determining the locations of recently expanded synapses throughout a nervous system is therefore an essential component in understanding neuronal circuitry formation and adaptation. While time-lapse microscopy can track synaptic growth in sparsely labeled neurons in superficial brain regions (Trachtenberg et al., 2002; Holtmaat et al., 2006), identifying growing synapses in deep regions of the brain or during unrestrained behavior has not been possible. A plausible strategy might be to selectively image newly synthesized proteins that preferentially accumulate in growing synapses. Evidence suggests that during synaptogenesis, PSD-95 accumulates in dendritic spines from a diffuse cytoplasmic pool (Li and Sheng, 2003). Furthermore, based on fluorescence recovery after photobleaching experiments, spines in differentiating hippocampal neurons appear to contain two populations of PSD-95 molecules, with 25-40% of PSD-95 protein exchanging with a half-time of minutes and the remainder relatively immobile (Nakagawa et al., 2004) (Sharma and Craig 2007).

Figure 3A:
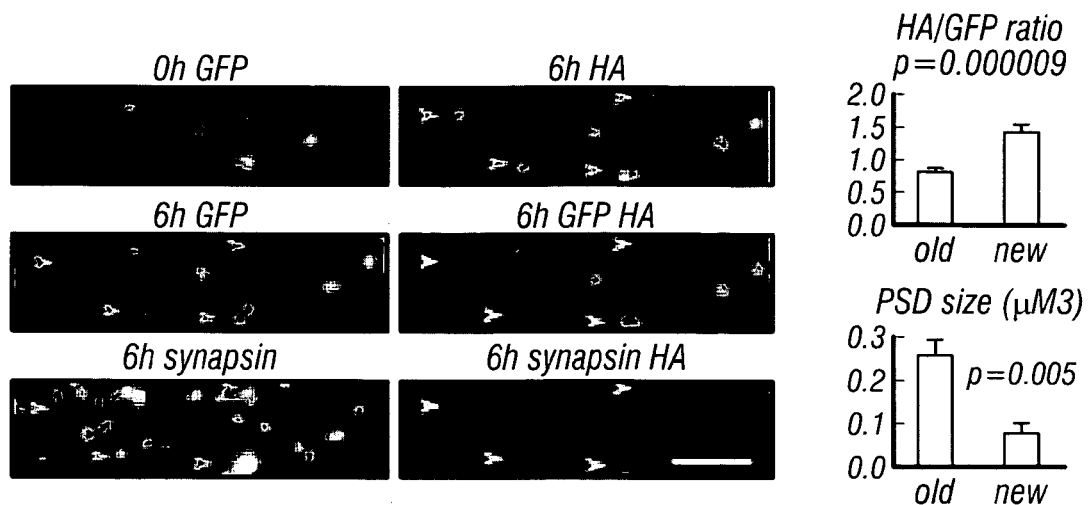
FIG. 3A-C shows newly forming synapses preferentially accumulate new PSD-95. (A) 21 DIV neurons at 14 DPT expressing PSD-95-GFP-TimeSTAMPa-HA were imaged at the time of BILN-2061 addition. After fixation 6 hours later, cells were stained for HA for newly synthesized PSD-95 and synapsin to verify the synaptic identity of PSD-95 puncta. Arrowheads mark new synapses as identified by comparison of images from the beginning and end of the experiment. New synapses show significantly higher mean HA/GFP intensity ratios and smaller size. (B) Synaptic size alone does not correlate with higher HA/GFP ratios, as stable synapses of different sizes (arrowheads) showed similar HA/GFP ratios. (C) Synaptic nascency correlates with the new PSD-95 fraction. 14 DIV neurons at 7 DPT were treated with BILN-2061 while GFP puncta formation was tracked by time-lapse microscopy, then neurons were fixed and stained for HA. Newly appearing puncta are marked by arrowheads. Asterisks track two preexisting mobile puncta. HA/GFP ratios of synapses are inversely correlated with their age (n=27). For all panels, data are represented as mean+/−SEM. HA/GFP ratios are in arbitrary units normalized to population mean. Maximal intensity projections of epifluorescence images spaced 0.5 µm through the neuron are shown. Scale bars, 5 µm.
Figure 3B:
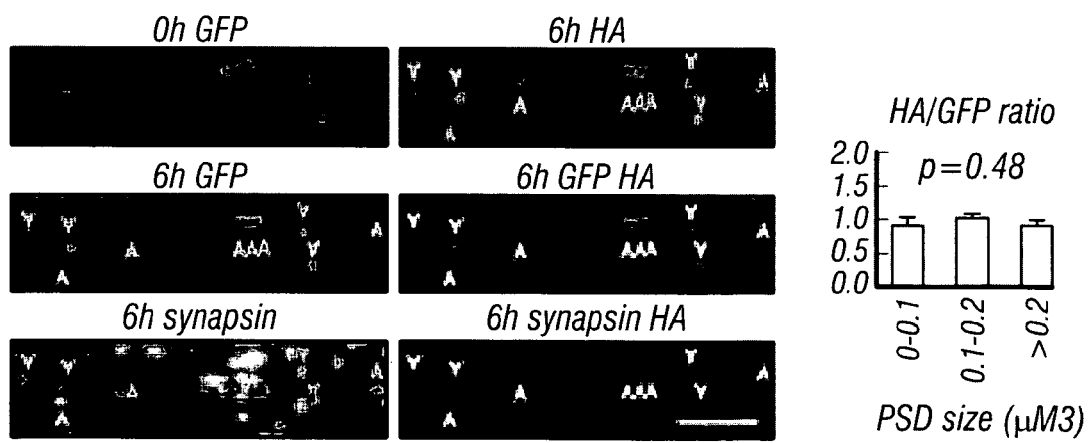
Figure 3C:
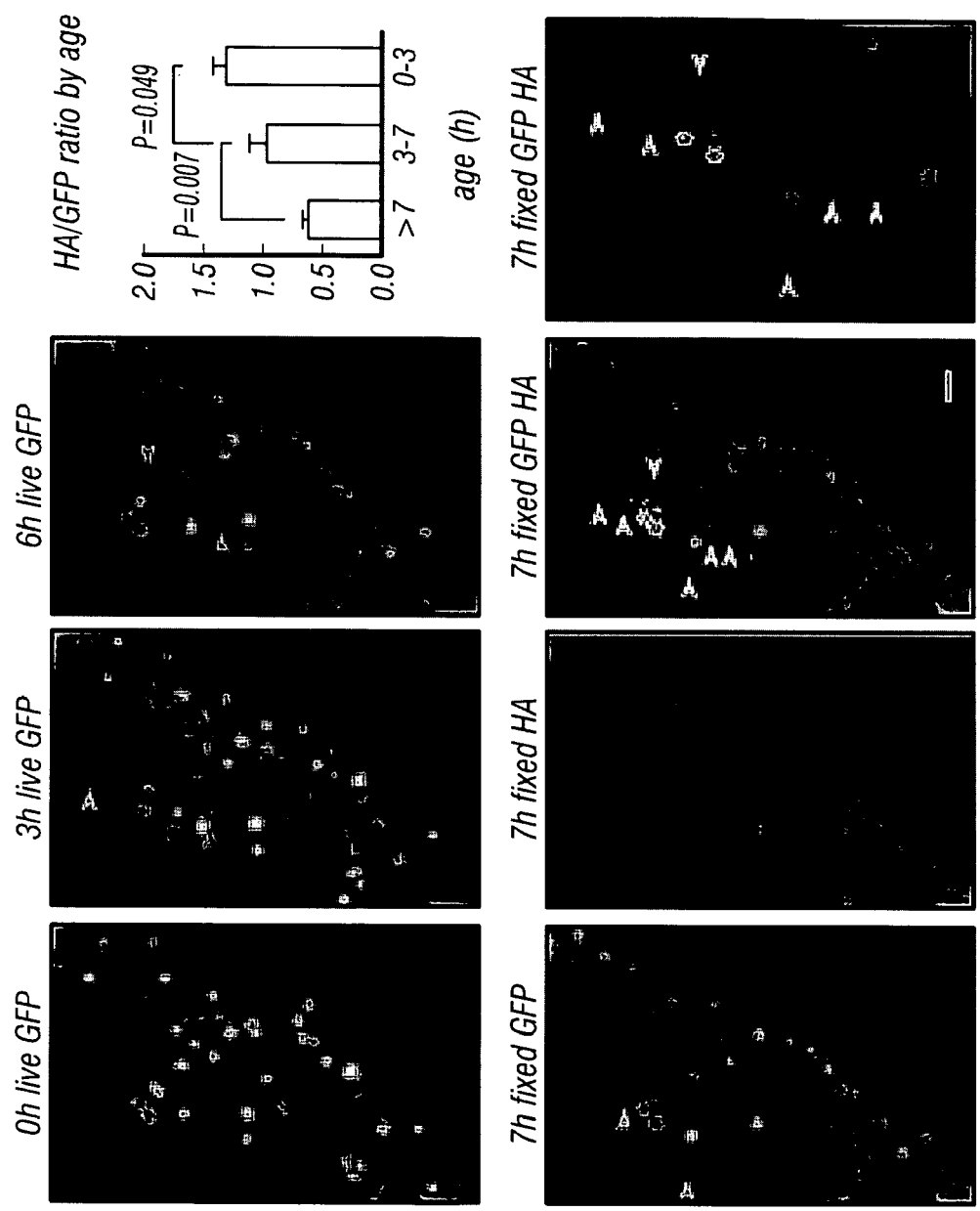

Given the evidence that a subpopulation of postsynaptic proteins is stably bound at synapses, the possibility that the presence of newly synthesized postsynaptic proteins could be used to identify nascent synapses, using PSD-95 as a model was examined. GFP images of neurons transfected with PSD-95-GFP-TimeSTAMPa-HA were acquired, followed by incubation with BILN-2061 for 6 hours to induce tag preservation on newly synthesized PSD-95. Upon comparison of GFP images from the beginning and the end of the 6 hour interval, new postsynaptic densities were identified as newly appearing PSD-95-GFP puncta that showed colocalization with the presynaptic marker synapsin (Ziv and Garner, 2004). These new postsynaptic densities showed significantly higher HA immunofluorescence relative to GFP intensity, indicating that they preferentially incorporate newly synthesized PSD-95 (FIG. 3A). New postsynaptic densities were also significantly smaller in size (FIG. 3A). However, small size alone is not a sufficient indicator of new synapses, as some neurons exhibited small postsynaptic densities at the end of the experiment that had not arisen during the observation period (FIG. 3B). These stable small postsynaptic densities also had similar HA/GFP ratios as nearby stable large postsynaptic densities (FIG. 3B), demonstrating that larger postsynaptic densities do not inherently demonstrate lower HA/GFP ratios, e.g. due to incomplete anti-HA antibody permeability in larger postsynaptic densities. By using closely spaced time-lapse intervals, the HA/GFP ratio was observed and correlated with the newness of the synapse, so that more recently appearing synapses had significantly higher HA/GFP ratios than those appearing earlier (FIG. 3C). These results show that a high fractional content of new PSD-95 characterizes newly born synapses. In all the experiments, old synapses were observed to maintain distinctly lower HA/GFP ratios than the adjacent dendritic shaft, confirming that synaptic PSD-95 molecules are not in complete and rapid exchange with the PSD-95 pool in the dendritic shaft. Taken together, these results raise the possibility that visualization of newly synthesized proteins by TimeSTAMP may be useful for the retrospective determination of synaptic birth order.

Whole-Brain Mapping of New Protein Distributions in Living Animals.

The ability of TimeSTAMP to be controlled by a cell-permeable drug should allow time-specific protein tagging in a living animal. To examine turnover analysis of the *Drosophila melanogaster* calcium/calmodulin-dependent protein kinase II (dCaMKII) was performed, whose transcription occurs throughout the nervous system (Takamatsu et al., 2003), but whose translation is induced by high levels of neuronal activity (Ashraf et al., 2006). As the CaMKII C-terminus mediates homododecamerization, CaMKII was taked at the N-terminus using a TimeSTAMPt module in which an HSV tag serves as the N-terminal drug-dependent epitope and the C-terminal HA tag as a constitutive epitope. The resulting HSV-TimeSTAMPt-HA-dCaMKII fusion protein demonstrates BILN-2061-dependent HSV tag preservation in transfected cells at room temperature (FIG. 6D). Transgenic flies were generated expressing this fusion protein in all neurons. By staining to the HA tag, the transgenically expressed dCaMKII protein was observed to be expressed throughout the brain with enrichment in the mushroom bodies (MBs), similar to the expression pattern of a co-expressed tubulin-GFP reporter (FIG. 4A). Strong HSV staining was observed in areas of dCaMKII expression when inhibitor was applied to flies, and no staining without inhibitor application (FIG. 4B). In similar experiments using the slower cleaving HSV-TimeSTAMPa-HA-dCaMKII construct, drug-dependent HSV staining was also observed, although faint staining was present in the absence of drug (FIG. 9). These experiments demonstrate that the TimeSTAMP cassette confers drug control over epitope tagging in living flies.

Figure 10A:
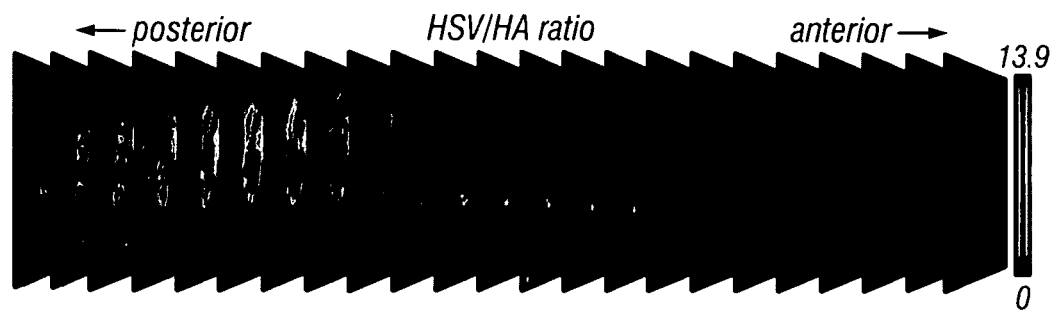
FIG. 10A-B shows that TimeSTAMP reveals tissue and subcellular locations of newly synthesized dCaMKII. (A) A 3-dimensional map of 6-hour fractional new dCaMKII was constructed in flies expressing HSV-TimeSTAMPt-HA-dCaMKII. Anti-HSV labels new dCaMKII and anti-HA labels total dCaMKII. HSV/HA ratiometric images are shown in pseudogray intensity-modulated display, scaled in arbitrary units relative to the mean whole-brain HSV/HA ratio. Individual confocal sections spaced 5 µm apart are shown. (B) HA staining of flies expressing HSV-TimeS-TAMPa-HA-dCaMKII shows total dCaMKII in Kenyon cell bodies and within the calyx, which is enriched in tubulin-GFP. HSV staining reveals recently synthesized dCaMKII is enriched in the cell bodies. A diagram of the left MB is in the top-left pane. Abbreviations: ped, peduncle; KCs, Kenyon cell bodies; ant, anterior; lat, lateral. Scale bar, 10 µm.

HSV/HA immunofluorescence intensity ratio was measured as a reflection of fractional new dCaMKII content throughout three-dimensional confocal reconstructions of brains from flies administered BILN-2061 for 6 hours (FIG. 10A). Hotspots of high HSV/HA values were seen in groups of Kenyon cell neurons located at the posterior of the MBs, and correlated with the presence of high concentrations of HSV-tagged new dCaMKII (FIG. 10A). Kenyon cells project axons through the peduncles that then branch in the $\alpha$, $\alpha'$, $\beta$, $\beta'$ and $\gamma$ lobes of the MBs. HSV staining and high HSV/HA values could be traced from the Kenyon cell bodies along discrete axonal bundles in the peduncle and were continuous with moderate HSV staining and HSV/HA values in the $\alpha$ and $\beta$ lobes (FIG. 10A). In contrast, no HSV staining was observed in the $\alpha'$, $\beta'$ and $\gamma$ lobes (FIG. 5B), even though total dCaMKII protein, as revealed by HA staining, is equally abundant in the $\alpha$, $\alpha'$, $\beta$, $\beta'$ and $\gamma$ lobes (FIG. 4, 5B). These results indicate that Kenyon cells projecting to the $\alpha$ and $\beta$ lobes maintain higher rates of dCaMKII synthesis than Kenyon cells projecting to the $\alpha'$, $\beta'$, and $\gamma$ lobes. Assuming steady-state levels of dCaMKII during the experiment, these results also imply that $\alpha/\beta$ Kenyon cells exhibit higher rates of dCaMKII degradation as well. Interestingly, $\alpha/\beta$ Kenyon cells represent a developmentally and functionally distinct population of Kenyon cells (Krashes et al., 2007; McGuire et al., 2001).

Figure 5A:
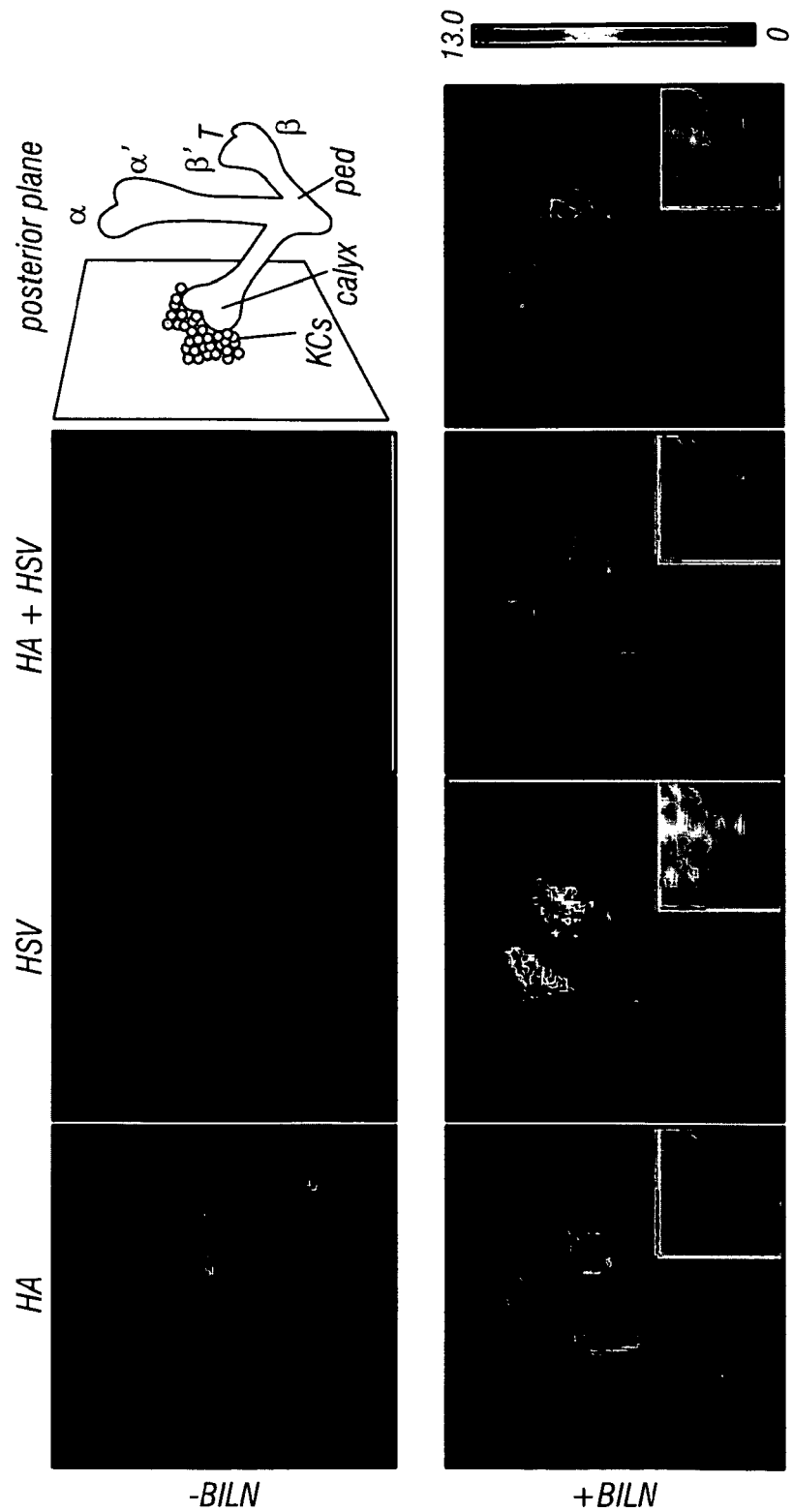
FIG. 5A-B shows high-resolution mapping of new dCaMKII distribution in vivo. (A) Kenyon cells are heterogeneous in dCaMKII production. Individual and merged images of anti-HSV and anti-HA staining are shown in the first 3 columns, and a HSV/HA ratiometric image is shown at right in pseudocolor intensity-modulated display, scaled in arbitrary units relative to the mean whole-brain HSV/HA ratio. A zoomed image of the boxed area is inset. Images are maximum intensity projections of two adjacent confocal sections. A diagram of the right MB is in the top-right. Abbreviations: ped, peduncle; KCs, Kenyon cell bodies. (B) Kenyon cells actively translating dCaMKII project to the α and β lobes, but not to the α', β', or γ lobes, and HSV/HA ratios are higher in the cell bodies than in the distal axons. Anti-HSV fluorescence intensity is scaled four-fold higher than in (B) for visibility, otherwise parameters are identical. Scale bars, 20 µm.
Figure 5B:
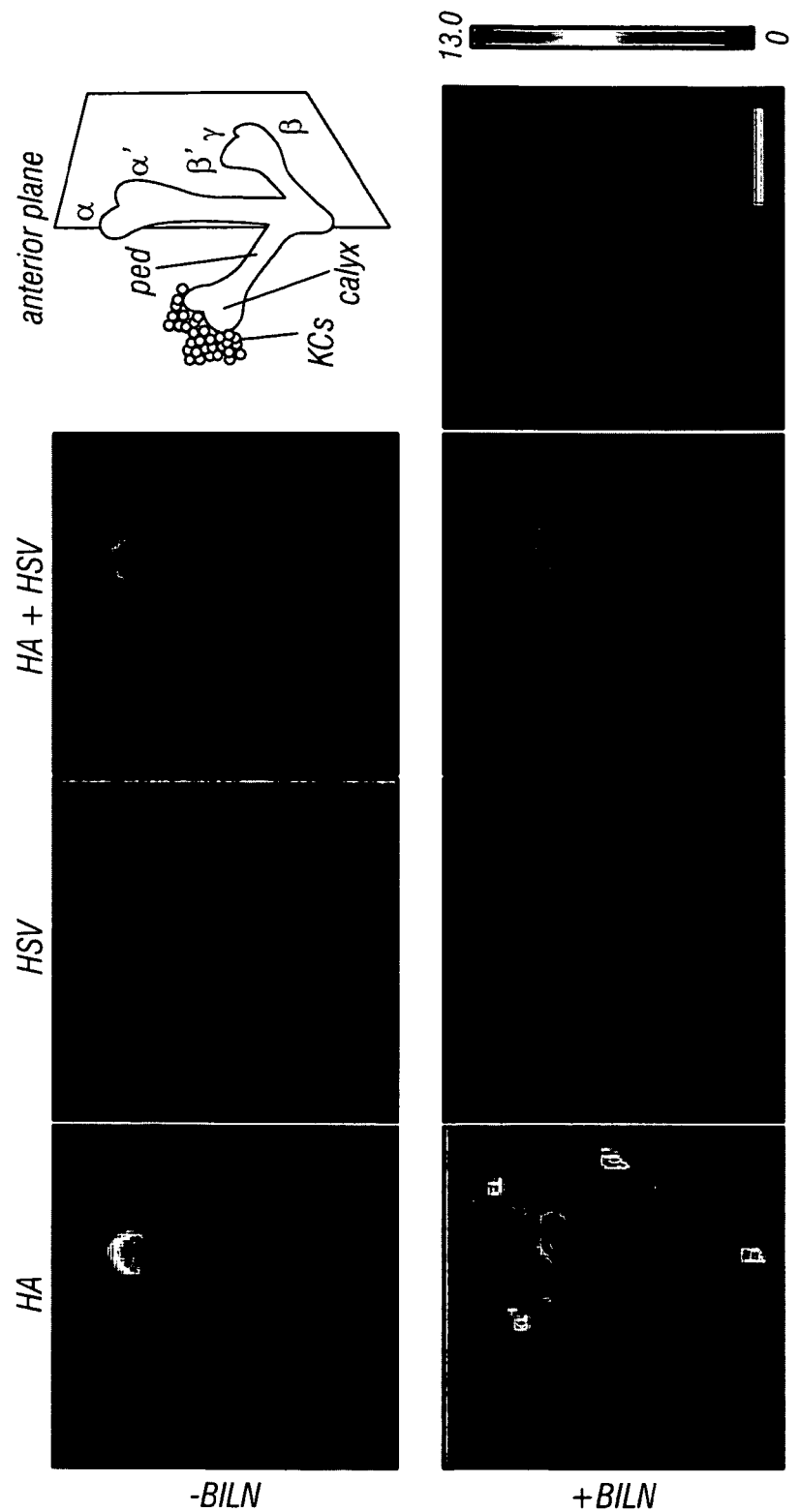
Figure 10B:
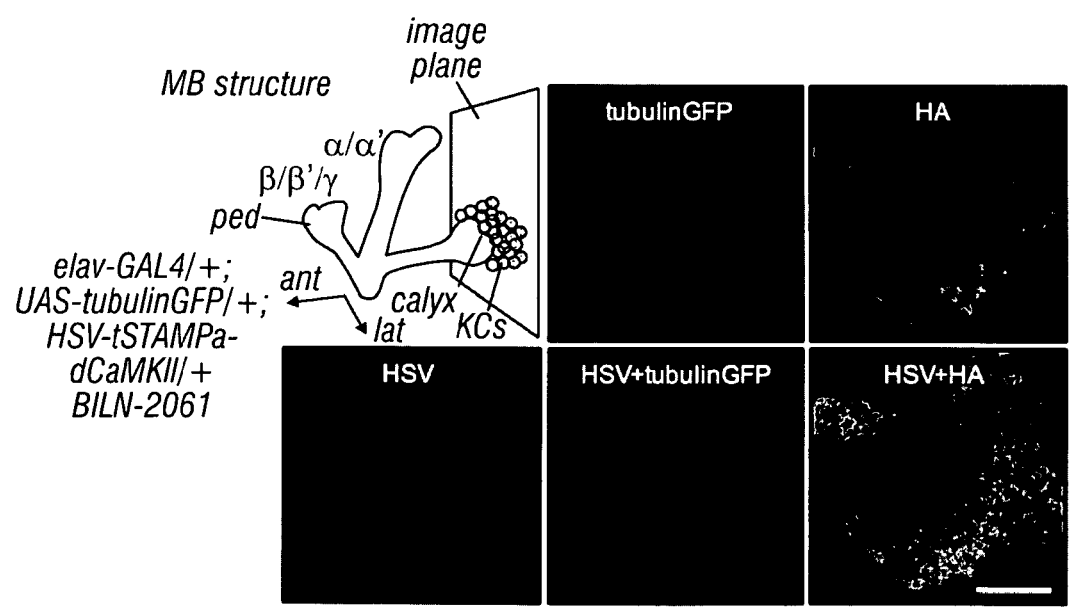

TimeSTAMP-mediated tagging also revealed subcellular differences in the distribution of newly synthesized proteins in neurons in the fly brain. Within Kenyon cells, HSV staining intensities and HSV/HA ratios are found in patterns complementary to that of total dCaMKII, with higher levels in the cell bodies and peduncle than in the distal axon branches within the lobes (FIG. 5). Similar results were obtained in flies expressing HSV-TimeSTAMPa-HA-dCaMKII (FIG. 10B). This pattern of dCaMKII turnover is consistent with dCaMKII production in the Kenyon cells occurring predominantly in the cell bodies. Taken together, these results show that the TimeSTAMP technique is able to reveal heterogeneity in dCaMKII production between neurons and in the trafficking of new dCaMKII molecules between subcellular regions in the brains of living animals.

Although a number of embodiments and features have been described above, it will be understood by those skilled in the art that modifications and variations of the described embodiments and features may be made without departing from the teachings of the disclosure or the scope of the disclosure as defined by the appended claims.

What is claimed is:

1. An isolated polynucleotide encoding a fusion polypeptide comprising:
   (i) a polypeptide of interest,
   (ii) a protease,
   (iii) a protease cleavable linker, and
   (iv) a tag moiety selected from the group consisting of a fluorescent moiety, a fluorescent moiety that undergoes FRET, a fragment of a fluorescent protein a bioluminescent moiety, a bioluminescent moiety that undergoes BRET, a fragment of a bioluminescent moiety, a peptide or protein that affects signal transduction or the cell cycle, a marker enzyme, a marker enzyme fragment, and a protein toxin,
   wherein each of (i)-(iv) are operably linked, and wherein the protease can be inhibited by contacting with a protease inhibitor.

2. An isolated polynucleotide comprising:
   a multiple cloning site;
   a nucleic acid encoding a first linker moiety;
   a nucleic acid encoding a protease;
   a nucleic acid encoding a second linker moiety; and
   a nucleic acid encoding a tag moiety,
wherein at least one of the first linker moiety or the second linker moiety is a protease cleavable linker, and wherein the protease can be inhibited by a protease inhibitor.

3. The isolated polynucleotide of claim 2, further comprising a nucleic acid encoding a polypeptide of interest.

4. The isolated polynucleotide of claim 2, wherein the first and second linker moieties comprise protease cleavable linker peptides.

5. The isolated polynucleotide of claim 2, wherein the first or second linker moiety comprises a protease cleavable linker peptide.

6. The isolated polynucleotide of claim 2, wherein the first and second linker moieties are the same.

7. A host cell transfected with the polynucleotide of claim 1 or 2.

8. A method of monitoring protein turnover or protein age of a polypeptide of interest, comprising
   (a) contact a cell or subject with a polynucleotide of claim 1,
   (b) measuring an amount of tag or a property of a tag in the cell or subject;
   (c) contacting the cell or subject with an inhibitor of the cleavable agent;
   (d) measuring an amount of tag or a property of a tag in the cell or subject after contacting with the cleavable agent; comparing the measurements of (b) and (d), wherein a change is indicative of protein turnover or protein age.

9. The method of claim 8, wherein the measuring is performed continuously over a period of time.

10. The method of claim 8, wherein the measuring is performed at repeated intervals over a period of time.

* * * * *